United States Patent
Freier

(10) Patent No.: US 7,632,824 B2
(45) Date of Patent: Dec. 15, 2009

(54) COMPOSITIONS AND METHODS FOR MODULATION OF MCL-1 EXPRESSION

(75) Inventor: Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 61 days.

(21) Appl. No.: 11/687,535

(22) Filed: Mar. 16, 2007

(65) Prior Publication Data

US 2007/0270368 A1 Nov. 22, 2007

Related U.S. Application Data

(60) Provisional application No. 60/783,505, filed on Mar. 16, 2006.

(51) Int. Cl.
*C07H 21/02* (2006.01)
*C07H 21/04* (2006.01)
*A61K 31/70* (2006.01)
*C12N 5/00* (2006.01)
*C12Q 1/68* (2006.01)

(52) U.S. Cl. .................. 514/44; 536/23.1; 536/24.1; 536/24.5; 435/6; 435/375; 435/377

(58) Field of Classification Search .................. None
See application file for complete search history.

(56) References Cited

U.S. PATENT DOCUMENTS

| | | | |
|---|---|---|---|
| 5,801,154 | A | 9/1998 | Baracchini et al. |
| 6,001,992 | A | 12/1999 | Ackermann et al. |
| 6,582,908 | B2 | 6/2003 | Fodor et al. |
| 6,800,750 | B1 | 10/2004 | Craig et al. |
| 7,250,496 | B2 * | 7/2007 | Bentwich .................. 536/23.1 |
| 2001/0053519 | A1 | 12/2001 | Fodor et al. |
| 2003/0228597 | A1 | 12/2003 | Cowsert et al. |

FOREIGN PATENT DOCUMENTS

| | | |
|---|---|---|
| WO | WO 94/29330 | 12/1994 |
| WO | WO 00/40595 | 7/2000 |
| WO | WO0177384 | * 10/2001 |

OTHER PUBLICATIONS

Aichberger et al., "Identification of mcl-1 as a BCR/ABL-dependent target in chronic myeloid leukemia (CML): evidence for cooperative antileukemic effects of imatinib and mcl-1 antisense oligonucleotides." Blood (2005) 105(8):3303-3311.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002,.
Crooke et al., "Basic Principles of Antisense Therapeutics" Antisense Research and Application (1998) Chapter 1:1-50.
Derenne et al., "Antisense strategy shows that Mcl-1 rather than Bcl-2 or Bcl-XL is an essential survival protein of human myeloma cells" Blood (2002) 100(1):194-199.
Henson et al., "Herceptin Sensitizes ErbB2—Overexpressing Cells to Apoptosis by Reducing Antiapoptotic Mcl-1 Expression" Clin. Cancer Res. (2006) 12(3):845-853.
Leuenroth et al., "The loss of Mcl-1 expression in human polymorphonuclear leukocytes promotes apoptosis" J. Leukoc. Biol. (2000) 68:158-166.
Liu et al., "Constitutively Actived Akt-1 Is Vital for the Survival of Human Monocyte-differentiated Macrophages: Role of Mcl-1, Independent of Nuclear Factor (NF)-kB, Bad, or Caspase Activation" J. Exp. Med. (2001) 194(2):113-126.
Michels et al., "Mcl-1 is required for Akata6 B-lymphoma cell survival and is converted to a cell death molecule by efficient caspase-mediated cleavage" Oncogene (2004) 23(28):4818-4827.
Moulding et al., "Apoptosis is rapidly triggered by antisense depletion of MCL-1 in differentiating U937 cells" Blood (2000) 96:1756-1763.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Selzer et al., "Betulinic Acid-induced Mcl-1 Expression in Humna Melanoma—Mode of Action and Functional Significance" Mol. Med. (2002) 8(12):877-884.
Sieghart et al., "Mcl-1 overexpression in hepatocellular carcinoma: A potential target for antisense therapy" J. Hepatol, (2006) 44(1):151-157.
Sly et al., "Survival of *Mycobacterium tuberculosis* in Host Macrophages Involves Resistance to Apoptosis Dependent upon Induction of Antiapoptotic Bcl-2 Family Member Mcl-1" J. Immunol. (2003) 170(1):430-437.
Song et al., "Mcl-1 Regulates Survival and Sensitivity to Diverse Apoptotic Stimuli in Human Non-Small Cell Lung Cancer Cells" Cancer Biol. Ther. (2005) 4(3):267-276.
Thallinger et al., "Mcl-1 Antisense Therapy Chemosensitizes Human Melanoma in a SCID Mouse Xenotransplantation Model" J. Invest. Dermatol. (2003) 120(6):1081-1086.
Thallinger et al., "Mcl-1 Is a Novel Therapeutic Target for Human Sarcoma: Synergistic Inhibition of Human Sarcoma Xenotransplants by a Combination of Mcl-1 Antisense Oligonucleotides with Low-Dose Cyclophosphamide" Clin. Cancer Res. (2004) 10:4185-4191.
Zhang et al., "Myeloid cell factor-1 is a critical survival factor for multiple myeloma" Blood (2002) 99(6):1885-1893.
International Search Report for PCT Application No. PCT/US2007/006706 dated Dec. 28, 2007.

* cited by examiner

*Primary Examiner*—Sean R McGarry
(74) *Attorney, Agent, or Firm*—Knobbe Martens Olson & Bear LLP

(57) ABSTRACT

Disclosed herein are compounds, compositions and methods for modulating the expression of Mcl-1 in a cell, tissue or animal. Also provided are methods of target validation. Also provided are uses of disclosed compounds and compositions in the manufacture of a medicament for treatment of diseases and disorders.

21 Claims, No Drawings

COMPOSITIONS AND METHODS FOR MODULATION OF MCL-1 EXPRESSION

CROSS-REFERENCE TO RELATED APPLICATIONS

This application is an non-provisional application of U.S. Provisional Patent Application No. 60/783,505, entitled COMPOSITIONS AND METHODS FOR MODULATION OF MCL-1 EXPRESSION, filed Mar. 16, 2006, the disclosure of which is incorporated herein by reference in its entirety.

REFERENCE TO SEQUENCE LISTING

The present application is being filed along with a Sequence Listing in electronic format. The Sequence Listing is provided as a file entitled BIOL0079-SEQ.TXT, created Mar. 16, 2007, which is 84.3 Kb in size. The information in the electronic format of the Sequence Listing is incorporated by reference in its entirety.

FIELD OF THE INVENTION

Disclosed herein are compounds, compositions and methods for modulating the expression of Mcl-1 in a cell, tissue or animal.

BACKGROUND

The Bcl-2 family of proteins, which plays an important role in regulating cell survival and cell death, can be divided into two groups, proapoptotic proteins (Bak and Bak) and antiapoptotic proteins (Bcl-2, Bcl-$x_L$, Al, Mcl-1, and Bcl-w) (Adams et al. (1998) *Science* 281:1322-1326; Henson et al. (2006) *Clin. Cancer Res.* 12(3):845-853). Antiapoptotic family member Mcl-1 was first characterized from a myeloid leukemia cell line (ML-1) induced to differentiate along the monocytic lineage (Kozopas et al. (1993) *Proc. Natl. Acad. Sci. U.S.A.* 90:3516-3520; Leuenroth et al. (2000) *J. Leukoc. Biol.* 68:158-166) and has since been shown to be expressed in a wide variety of tissues and neoplastic cells and to influence the development of numerous malignancies (Thallinger et al. (2004) *Clin. Cancer Res.* 10:4185-4191).

The role of Mcl-1 in regulating cell fate has made it a target of interest in many studies of apoptosis and hyperproliferative diseases. Many reports have demonstrated the importance of inhibiting Mcl-1 expression to increase apoptosis and regulate neoplastic disease.

U.S. Pat. No. 6,001,992 discloses antisense oligonucleotides for inhibition of expression of anti-apoptotic bcl-2 related proteins, including Mcl-1.

U.S. Pat. No. 6,800,750 discusses Mcl-1 regulatory elements, oligonucleotide primers which hybridize to Mcl-1 and methods of modulating apoptosis of a cell by modulating expression of Mcl-1.

WO 94/29330 discloses Mcl-1 polypeptide and polynucleotide sequences and discusses methods of treating a subject having a cell proliferative disorder.

Several studies have reported use of Mcl-1 antisense oligonucleotides or siRNA to inhibit Mcl-1 expression, increase apoptosis, decrease cell viability and/or decrease tumor weight of normal cells, cancer cell lines or xenograft tumors. Henson et al. ((2006) *Clin. Cancer Res.* 12(3):845-853) disclose a Mcl-1 antisense oligonucleotide which sensitizes breast cancer cell lines to apoptosis. Selzer et al. ((2002) *Mol. Med.* 8(12):877-884) disclose inhibition of Mcl-1 expression in melanoma cells using an antisense oligonucleotide targeting Mcl-1 and Skvara et al. ((2005) *Anticancer Res.* 25(4): 2697-2703) show a Mcl-1 antisense oligonucleotide which sensitizes human melanoma cells to ionizing radiation-induced apoptosis. Sieghart et al. ((2006) *J. Hepatol.* 44(1): 151-157) discuss the finding the Mcl-1 is overexpressed in hepatocellular carcinoma cells lines and disclose a Mcl-1 antisense oligonucleotide which decreases protein expression, increases apoptosis, decreases cell survival and sensitizes HCC cells to chemotherapy. Similarly, Song et al. ((2005) *Cancer Biol. Ther.* 4(3):267-276) show that Mcl-1 is overexpressed in human lung cancer cells and treatment with a Mcl-1 antisense oligonucleotide resulted in an increase in apoptosis. Mcl-1 inhibition also caused sensitization of the lung cancer cells to apoptosis induced by chemotherapeutic agents and radiation.

Aichberger et al. ((2005) *Blood* 105(8):3303-3011) discuss a Mcl-1 antisense oligonucleotide and siRNA which inhibit expression of Mcl-1 in chronic myeloid leukemia cells and decreased cell viability. Mcl-1 antisense oligonucleotide synergized with the BCR/ABL inhibitor Imatinib to produce growth arrest. Derenne et al. ((2002) *Blood* 100(1):194-199) and Zhang et al. ((2002) *Blood* 99(6):1885-1893) discuss use of Mcl-1 antisense oligonucleotide to decrease expression of Mcl-1, decrease cell viability and increase apoptosis of multiple myeloma cells lines and primary cells.

Mcl-1 has also been shown to exhibit increased expression in a variety of hematopoietic cells lines, including B cells, monocytes, macrophages and polymorphonuclear cells, and treatment of these cells with Mcl-1 antisense oligonucleotide reduces target expression and increases apoptosis (Michels et al. (2004) *Oncogene* 23(28):4818-4827; Sly et al. (2003) *J. Immunol.* 170(1):430-437; Liu et al. (2001) *J. Exp. Med.* 194(2):113-126; Moulding et al. (2000) *Blood* 96(5):1756-1763; and Leuenroth et al. (2000) *J Leukoc. Biol.* 68:158-166).

Thallinger et al. ((2004) *Clin. Cancer Res.* 10:4185-4191) disclose an antisense oligonucleotide targeted to Mcl-1 which decreases expression of Mcl-1 in sarcoma xenotransplants and when used in combination with cyclophosphamide, reduces tumor weight and increases tumor cell apoptosis. Thallinger et al. ((2003) *J. Invest. Dermatol.* 120(6):1081-1086) show a Mcl-1 antisense oligonucleotide administered systemically with or without dacarbazine in a human melanoma SCID mouse xenotransplantation model decreased target protein expression, increased apoptosis and decreased tumor weight.

Given the role of Mcl-1 in a variety of disorders, including hyperproliferative disorders, an efficient method of modulating expression of Mcl-1 is desirable. Antisense technology is an effective means for reducing the expression of one or more specific gene products and is uniquely useful in a number of therapeutic, diagnostic, and research applications. Provided herein are antisense compounds for use in modulation of Mcl-1 expression.

SUMMARY

Provided herein are oligomeric compounds targeting Mcl-1. Also provided are methods of modulating expression of Mcl-1 in cells, tissue or animals using oligomeric compounds targeting Mcl-1. Further provided are methods of increasing apoptosis and methods of decreasing cell proliferation using said compounds.

In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. An oligomeric compound 12 to 50 nucleobases in length comprising at least an 8-nucleobase portion of a sequence selected from the group consisting of SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 and 120.

2. The compound of paragraph 1 which is 20 nucleobases in length and has a sequence selected from the group consisting of SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 and 120.

3. The compound of paragraph 1 comprising at least an 8-nucleobase portion of a sequence selected from the group consisting of SEQ ID NO: 64, 86, 87, 92, 95 and 96.

4. The compound of paragraph 3 having a sequence selected from the group consisting of SEQ ID NO: 64, 86, 87, 92, 95 and 96.

5. The compound of paragraph 1 which is at least 80% complementary to a nucleic acid molecule encoding human Mcl-1.

6. The compound of paragraph 5 which is at least 90% complementary to a nucleic acid molecule encoding human Mcl-1.

7. The compound of paragraph 6 which is at least 95% complementary to a nucleic acid molecule encoding human Mcl-1.

8. The compound of paragraph 7 which is 100% complementary to a nucleic acid molecule encoding human Mcl-1.

9. The compound of any one of paragraphs 5-8 wherein the nucleic acid molecule is selected from the group consisting of SEQ ID NO: 1, 2, 3, 4 and 5.

10. An oligomeric compound 16 to 50 nucleobases in length having at least 80% identity with SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120.

11. The compound of paragraph 10 which is 17 to 50 nucleobases in length and has at least 85% identity with SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120.

12. The compound of paragraph 10 which is 18 to 50 nucleobases in length and has at least 90% identity with SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120.

13. The compound of paragraph 10 which is 19 to 50 nucleobases in length and has at least 95% identity with SEQ ID NO: 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120.

14. An oligomeric compound 12 to 50 nucleobases in length targeted to a nucleic acid molecule encoding human Mcl-1 (SEQ ID NO: 2), wherein said compound specifically hybridizes to at least a portion of a target region defined by nucleobases 123-150; 719-748; 808-839; 902-930; 902-1007; 938-1007; 1039-1074; 1083-1150; 1104-1128; 1252-1297; 1396-1423; 1651-1693; 1809-1851; 2062-2103; 2551-2585; 3118-3161; 3176-3202; or 3214-3254 of said nucleic acid molecule encoding human Mcl-1.

15. The compound of any one of paragraphs 1, 3, 5, 6, 7 or 14 which is 15 to 30 nucleobases in length.

16. The compound of any of paragraphs 1-15 comprising at least one modified sugar moiety, internucleoside linkage or nucleobase.

17. The compound of paragraph 16, wherein the modified sugar moiety is 2'-O-methoxyethyl.

18. The compound of paragraph 16, wherein the modified nucleobase is phosphorothioate.

19. The compound of paragraph 16, wherein the modified nucleobase is 5-methylcytosine.

20. A method of modulating expression of human Mcl-1 in a cell, tissue or animal, comprising administering to said cell, tissue or animal the oligomeric compound of any one of paragraphs 1-19.

21. A method of inducing apoptosis of a cell, comprising administering to said cell the oligomeric compound of any one of paragraphs 1-19.

22. A method of inhibiting proliferation of a cell, comprising administering to said cell the oligomeric compound of any one of paragraphs 1-19.

23. A compound according to any one of paragraphs 1-19 for use in therapy.

24. Use of a compound according to any one of paragraphs 1-19 for the preparation of a medicament for modulating expression of human Mcl-1.

25. Use of a compound according to any one of paragraphs 1-19 for the preparation of a medicament for inducing apoptosis.

26. Use of a compound according to any one of paragraphs 1-19 for the preparation of a medicament for inhibiting cellular proliferation.

27. The use of any one of paragraphs 24-26, wherein the modulating, inducing or inhibiting occurs in a human cell.

DETAILED DESCRIPTION

Antisense technology is an effective means for reducing the expression of one or more specific gene products and is uniquely useful in a number of therapeutic, diagnostic, and research applications. Provided herein are antisense compounds useful for modulating gene expression and associated pathways via antisense mechanisms of action based on target degradation or target occupancy.

The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

Mcl-1 is known to play a significant role in cell viability. Overexpression of Mcl-1 has been associated with a variety of hyperproliferative disorders, including cancer (such as, for example, sarcomas, myelomas, melanomas, lymphomas, leukemias and carcinomas) and autoimmune disease (such as, for example, rheumatoid arthritis). Identification of compounds to modulate of Mcl-1 expression is critical. Thus, provided herein are antisense compounds targeting Mcl-1 which modulate expression of MC1-1.

As used herein, the terms "target nucleic acid" and "nucleic acid molecule encoding Mcl-1" have been used for convenience to encompass DNA encoding Mcl-1, RNA (including pre-mRNA and mRNA or portions thereof) transcribed from such DNA, and also cDNA derived from such RNA.

As used herein, "targeting" or "targeted to" refer to the process of designing an oligomeric compound such that the compound hybridizes with a selected nucleic acid molecule.

As used herein, "hybridization" means the pairing of complementary strands of oligomeric compounds. In the context of the present invention, an oligomeric compound is specifically hybridizable when there is a sufficient degree of complementarity to avoid non-specific binding of the oligomeric compound to non-target nucleic acid sequences.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

In accordance with the present invention are compositions and methods for modulating the expression of Mcl-1 (also known as Myeloid cell differentiation protein-1). Listed in Table 1 are GENBANK® accession numbers of sequences used to design oligomeric compounds targeted to Mcl-1. Oligomeric compounds of the invention include oligomeric compounds which hybridize with one or more target nucleic acid molecules shown in Table 1, as well as oligomeric compounds which hybridize to other nucleic acid molecules encoding Mcl-1. The oligomeric compounds may target any region, segment, or site of nucleic acid molecules which encode Mcl-1. Suitable target regions, segments, and sites include, but are not limited to, the 5'UTR, the start codon, the stop codon, the coding region, the 3'UTR, the 5' cap region, introns, exons, intron-exon junctions, exon-intron junctions, and exon-exon junctions.

TABLE 1

Gene Target Names and Sequences

| Target Name | Species | Genbank ® # | SEQ ID NO |
|---|---|---|---|
| Mcl-1 | Human | L08246.1 | 1 |
| Mcl-1 | Human | NM_021960.3 | 2 |
| Mcl-1 | Human | NM_182763.1 | 3 |
| Mcl-1 | Human | Complement of AI439011.1 | 4 |
| Mcl-1 | Human | Complement of NT_004487.17 (nucleotides 1036000 to 1044000) | 5 |
| Mcl-1 | Mouse | BC005427.1 | 6 |
| Mcl-1 | Mouse | NM_008562.2 | 7 |
| Mcl-1 | Mouse | NT_039238.1 (nucleotides 1444531 to 1448899) | 8 |
| Mcl-1 | Mouse | NT_039238.3 (nucleotides 3538000 to 3546000) | 9 |
| Mcl-1 | Mouse | U35623.1 | 10 |

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 12 to 50 nucleobases. One having ordinary skill in the art will appreciate that this embodies antisense compounds of 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 12 to 30 nucleobases. One having ordinary skill in the art will appreciate that this embodies antisense compounds of 12, 13, 14, 15, 16, 17, 18, 19, 20, 21, 22, 23, 24, 25, 26, 27, 28, 29 or 30 nucleobases.

In some embodiments, the antisense compounds of the invention comprise 15 to 30 nucleobases. One having ordinary skill in the art will appreciate that this embodies antisense compounds of 15, 16, 17, 18, 19, 20, 21, 22, 23, 24, 25, 26, 27, 28, 29 or 30 nucleobases.

In one embodiment, the antisense compounds of the invention comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds of the invention comprise 20 to 24 nucleobases. One having ordinary skill in the art will appreciate that this embodies antisense compounds of 20, 21, 22, 23, or 24 nucleobases.

In one embodiment, the antisense compounds of the invention comprise 16 to 20 nucleobases. One having ordinary skill in the art will appreciate that this embodies antisense compounds of 16, 17, 18, 19 or 20 nucleobases.

In one embodiment, the antisense compounds of the invention comprise 20 nucleobases.

In one embodiment, the antisense compounds of the invention comprise 19 nucleobases.

In one embodiment, the antisense compounds of the invention comprise 18 nucleobases.

In one embodiment, the antisense compounds of the invention comprise 17 nucleobases.

In one embodiment, the antisense compounds of the invention comprise 16 nucleobases.

In one embodiment, the antisense compounds of the invention comprise 15 nucleobases.

In one embodiment, the antisense compounds of the invention comprise 14 nucleobases.

In one embodiment, the antisense compounds of the invention comprise 13 nucleobases.

Antisense compounds 8-80 nucleobases in length, and any length within the range, comprising a stretch of at least eight (8) consecutive nucleobases selected from within the illustrative antisense compounds are considered to be suitable antisense compounds.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

One having skill in the art armed with the antisense compounds illustrated herein will be able, without undue experimentation, to identify further antisense compounds.

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least 70%, or at least 75%, or at least 80%, or at least 85%, or at least 90%, or at least 92%, or at least 95%, or at least 97%, or at least 98%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489).

Oligomeric compounds, or a portion thereof, may have a defined percent identity to a SEQ ID NO, or a compound having a specific ISIS number. The oligomeric compounds of the present invention may have, for example, 80%, 85%, 90%, 95% or 100% identity with a specified compound. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO). It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (i.e., one base replaced with another) versions of the oligonucleotides taught herein fall within the scope of the invention. Percent identity is calculated according to the number of bases that are identical to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. In the context of the invention, the full length of the modified sequence may constitute a single portion.

The oligomeric compounds of the invention also include compounds in which a different base is present at one or more of the nucleotide positions in the compound. For example, if the first nucleotide is an adenosine, compounds may be produced which contain thymidine, guanosine or cytidine at this position. This may be done at any of the positions of the oligomeric compound. These compounds are then tested using the methods described herein to determine their ability to inhibit expression of Mcl-1 mRNA.

As used herein, "targeting" or "targeted to" refer to the process of designing an oligomeric compound such that the compound hybridizes with a selected nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding Mcl-1" encompass DNA encoding Mcl-1, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes Mcl-1.

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Target regions may include, for example, a particular exon or intron, or may include only selected nucleobases within an exon or intron which are identified as appropriate target regions. In some instances, an appropriate target region is defined by the range of nucleobases of a target nucleic acid to which one or more overlapping oligomeric compounds hybridize. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5'CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds of the invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of oligomeric compounds useful of the present invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds can have one or more modified internucleoside linkages. Modified oligonucleotide backbones containing a phosphorus atom therein include, for example, phosphorothioates, chiral phosphorothioates, phosphorodithioates, phosphotri-esters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be a basic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Oligomeric compounds may also contain one or more substituted sugar moieties. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$OCH_3, O($CH_2$)$_n$NH_2, O($CH_2$)$_n$CH_3, O($CH_2$)$_n$ONH_2, and O($CH_2$)$_n$ON(($CH_2$)$_n$CH_3)$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH_3, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504), i.e., an alkoxyalkoxy group. A further modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—($CH_2$)$_2$—O—($CH_2$)$_2$—N($CH_3$)$_2$, also described in examples hereinbelow.

Other modifications include 2'-methoxy (2'-O—$CH_3$), 2'-aminopropoxy (2'-OCH_2CH_2CH_2NH_2), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger et al., Principles of Nucleic Acid Structure, 1984, Springer-Verlag; New York, N.Y.). As used herein, B-form geometry is inclusive of both C2'-endo pucker and O4'-endo pucker.

The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). Consequently, compounds that favor an A-form geometry can enhance stacking interactions, thereby increasing the relative Tm and potentially enhancing a compound's antisense effect.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Another group of oligomeric compounds includes oligonucleotide mimetics. The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., *Science,* 1991, 254, 1497-1500). PNAs have favorable hybridization properties, high biological stability and are electrostatically neutral molecules. PNA compounds have been used to correct aberrant splicing in a transgenic mouse model (Sazani et al., *Nat. Biotechnol.,* 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, *Biochemistry,* 2002, 41(14), 4503-4510). Morpholino-based oligomeric compounds have been studied in zebrafish embryos (see: *Genesis,* volume 30, issue 3, 2001 and Heasman, J., *Dev. Biol.,* 2002, 243, 209-214). Further studies of morpholino-based oligomeric compounds have also been reported (Nasevicius et al., *Nat. Genet.,* 2000, 26, 216-220; and Lacerra et al., *Proc. Natl. Acad. Sci.,* 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No.

5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. LNAs are commercially available from ProLigo (Paris, France and Boulder, Colo., USA).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA:LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-alpha-L-threose nucleic acid was prepared and compared to the 2' and 3' amidate analogs (Wu et al., *Organic Letters*, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta*, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido (5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941; and 5,750,692.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° C. relative to 5-methyl cytosine (dC5$^{me}$), which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenyl-butazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single-or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, (5'-O-(4,4'-Dimethoxytriphenylmethyl)-2'-O-(2-methoxyethyl)-$N^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research*, 1993, 21, 3197-3203) using commercially available phosphoramidites (Glen Research, Sterling Va. or Chem-Genes, Needham, Mass.).

2'-fluoro oligonucleotides can be synthesized routinely as described (Kawasaki, et. al., *J. Med. Chem.*, 1993, 36, 831-841) and U.S. Pat. No. 5,670,633.

2'-O-Methoxyethyl-substituted nucleoside amidites can be prepared routinely as per the methods of Martin, P., *Helvetica Chimica Acta*, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P=S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Patent, U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262, 6,559,279 and 6,762,281.

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

A large number of 2'-O-protecting groups have been used for the synthesis of oligoribonucleotides and any can be used. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese et al. have identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach is to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group, initially used for the synthesis of oligoribo-nucleotides, is the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal. For example, the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—CH$_2$—O—Si(iPr)$_3$, TOM). One 2'-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

The main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(2-Methoxyethyl)) Chimeric Phosphorothioate Oligonucleotides (2'-O-(2-methoxyethyl))-(2'-deoxy)-(–2'-O-(2-methoxyethyl)) chimeric phosphorothioate oligonucleotides can be prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl) Phosphodiester) Chimeric Oligonucleotides (2'-O-(2-methoxyethyl phosphodiester)-(2'-deoxy phosphorothioate)-(2'-O-(methoxyethyl) phosphodiester) chimeric oligonucleotides can be prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Methods of oligonucleotide purification and analysis are known to those skilled in the art. Analysis methods include capillary electrophoresis (CE) and electrospray-mass spectroscopy. Such synthesis and analysis methods can be performed in multi-well plates.

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of Mcl-1. Thus, in one embodiment modulation of expression can mean increase or decrease in target RNA or protein levels. In another embodiment modulation of expression can mean an increase or decrease of one or more RNA splice products, or a change in the ratio of two or more splice products.

Modulation of Mcl-1 expression can be assayed in a variety of ways known in the art. Mcl-1 mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by Mcl-1 can be quantitated in a variety of ways well known in the art, such as immunoprecipitation, Western blot analysis (immunoblotting), ELISA or fluorescence-activated cell sorting (FACS). Antibodies directed to a protein encoded by Mcl-1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Once one or more target regions, segments or sites have been identified, oligomeric compounds are designed which are sufficiently complementary to the target, i.e., hybridize sufficiently well and with sufficient specificity, to give the desired effect. The oligomeric compounds of the present invention can be targeted to features of a target nucleobase sequence.

The locations on the target nucleic acid to which active oligomeric compounds hybridize are hereinbelow referred to as "validated target segments." As used herein the term "validated target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). Similarly validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

In another embodiment, the validated target segments identified herein can be employed in a screen for additional compounds that modulate the expression of Mcl-1. "Modulators" are those compounds that modulate the expression of Mcl-1 and which comprise at least an 8-nucleobase portion which is complementary to a validated target segment. The screening method comprises the steps of contacting a validated target segment of a nucleic acid molecule encoding Mcl-1 with one or more candidate modulators, and selecting for one or more candidate modulators which perturb the expression of a nucleic acid molecule encoding Mcl-1. Once it is shown that the candidate modulator or modulators are capable of modulating the expression of a nucleic acid molecule encoding Mcl-1, the modulator can then be employed in further investigative studies of the function of Mcl-1, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

The oligomeric compounds of the present invention can be utilized for diagnostics, therapeutics, prophylaxis and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Compounds of the invention can be used to modulate the expression of Mcl-1 in an animal, such as a human. In one non-limiting embodiment, the methods comprise the step of administering to said animal an effective amount of an antisense compound that inhibits expression of Mcl-1. In one embodiment, the antisense compounds of the present invention effectively inhibit the levels or function of Mcl-1 RNA. Because reduction in Mcl-1 mRNA levels can lead to alteration in Mcl-1 protein products of expression as well, such resultant alterations can also be measured. Antisense compounds of the present invention that effectively inhibit the levels or function of Mcl-1 RNA or protein products of expression are considered active antisense compounds. In one embodiment, the antisense compounds of the invention inhibit the expression of Mcl-1 causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of Mcl-1 can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding Mcl-1 protein and/or the Mcl-1-encoded protein itself. For example, fluids, tissues or organs procured from an animal can be evaluated for expression levels of the target mRNA or protein. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds of the present invention can be utilized in pharmaceutical compositions by adding an effective amount of a compound to a suitable pharmaceutically acceptable diluent or carrier. In one aspect, the compounds of the present invention inhibit the expression of Mcl-1. The compounds of the invention can also be used in the manufacture of a medicament for the treatment of diseases and disorders related to Mcl-1 expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of Mcl-1 expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

The oligomeric compounds of the invention may also be formulated with active or inert ingredients, or a combination of both, for delivery via parenteral and non-parenteral routes of administration. Compositions and methods of preparing formulations are well known to those skilled in the art.

While certain compounds, compositions and methods of the present invention have been described with specificity in accordance with certain embodiments, the following examples serve only to illustrate the compounds of the invention and are not intended to limit the same. Each of the references, GENBANK® accession numbers, and the like recited in the present application is incorporated herein by reference in its entirety.

EXAMPLE 1

Cell Culture and Treatment with Oligomeric Compounds

The effect of oligomeric compounds on target nucleic acid expression was tested in A549 and b.END cells. The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in oligomeric compound transfection experiments.

The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

When cells reached appropriate confluency, they were treated with oligonucleotide using Lipofectin™ as described. When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 μg/mL per 100 nM oligonucleotide. This transfection mixture was incubated at room temperature for approximately 0.5 hours. For cells grown in 96-well plates, wells were washed once with 100 μL OPTI-MEM™-1 and then treated with 130 μL of the transfection mixture. Cells grown in 24-well plates or other standard tissue culture plates were treated similarly, using appropriate volumes of medium and oligonucleotide. Cells were treated and data were obtained in duplicate or triplicate. After approximately 4-7 hours of treatment at 37° C., the medium containing the transfection mixture was replaced with fresh culture medium. Cells were harvested 16-24 hours after oligonucleotide treatment.

Control oligonucleotides were used to determine the optimal oligomeric compound concentration for a particular cell line. Furthermore, when oligomeric compounds of the invention were tested in oligomeric compound screening experiments or phenotypic assays, control oligonucleotides were tested in parallel with compounds of the invention. In some embodiments, the control oligonucleotides were used as negative control oligonucleotides, i.e., as a means for measuring the absence of an effect on gene expression or phenotype. In alternative embodiments, control oligonucleotides were used as positive control oligonucleotides, i.e., as oligonucleotides known to affect gene expression or phenotype. Control oligonucleotides are shown in Table 2. "Target Name" indicates the gene to which the oligonucleotide is targeted. "Species of Target" indicates species in which the oligonucleotide is perfectly complementary to the target mRNA. "Motif" is indicative of chemically distinct regions comprising the oligonucleotide. The compounds in Table 2 are chimeric oligonucleotides, composed of a central "gap" region consisting of 2'-deoxynucleotides, which is flanked on both sides (5' and 3') by "wings". The wings are composed of 2'-O-(2-methoxyethyl) nucleotides, also known as 2'-MOE nucleotides. The "motif" of each gapmer oligonucleotide is illustrated in Table 2 and indicates the number of nucleotides in each gap region and wing, for example, "5-10-5" indicates a gapmer having a 10-nucleotide gap region flanked by 5-nucleotide wings. Similarly, the motif "5-9-6" indicates a 9-nucleotide gap region flanked by 5-nucleotide wing on the 5' side and a 6-nucleotide wing on the 3' side. ISIS 29848 is a mixture of randomized oligomeric compounds, where each nucleotide can be A, T, C or G. For each compound listed in Table 2, the internucleoside (backbone) linkages are phosphorothioate throughout the oligonucleotide. Unmodified cytosines are indicated by "C" in the nucleotide sequence; all other cytosines are 5-methylcytosines.

TABLE 2

Control oligonucleotides for cell line testing, oligomeric compound screening and phenotypic assays

| ISIS # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 11 |
| 289865 | forkhead box 01A (rhabdomyosarcoma) | Human | GGCAACGTGAACAGGTCCAA | 5-10-5 | 12 |
| 25237 | integrin beta 3 | Human | GCCCATTGCTGGACATGC | 4-10-4 | 13 |
| 196103 | integrin beta 3 | Human | AGCCCATTGCTGGACATGCA | 5-10-5 | 14 |
| 148715 | Jagged 2 | Human; Mouse; Rat | TTGTCCCAGTCCCAGGCCTC | 5-10-5 | 15 |
| 18076 | Jun N-Terminal Kinase - 1 | Human | CTTTC"CGTTGGA"C"CCCTGGG | 5-9-6 | 16 |

TABLE 2-continued

Control oligonucleotides for cell line testing,
oligomeric compound screening and phenotypic assays

| ISIS # | Target Name | Species of Target | Sequence (5' to 3') | Motif | SEQ ID NO |
|---|---|---|---|---|---|
| 18078 | Jun N-Terminal Kinase - 2 | Human | GTGCG"CG"CGAG"C"C"CGAAATC | 5-9-6 | 17 |
| 183881 | kinesin-like 1 | Human | ATCCAAGTGCTACTGTAGTA | 5-10-5 | 18 |
| 29848 | none | none | NNNNNNNNNNNNNNNNNNNN | 5-10-5 | 19 |
| 226844 | Notch (Drosophila) homolog 1 | Human; Mouse | GCCCTCCATGCTGGCACAGG | 5-10-5 | 20 |
| 105990 | Peroxisome proliferator-activated receptor gamma | Human | AGCAAAAGATCAATCCGTTA | 5-10-5 | 21 |
| 336806 | Raf kinase C | Human | TACAGAAGGCTGGGCCTTGA | 5-10-5 | 22 |
| 15770 | Raf kinase C | Mouse; Murine sarcoma virus; Rat | ATGCATT"CTG"C"C"C"C"CAAGGA | 5-10-5 | 23 |

The concentration of oligonucleotide used varies from cell line to cell line. To determine the optimal oligonucleotide concentration for a particular cell line, the cells were treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 µM to 40 µM when the antisense oligonucleotide is transfected by electroporation.

EXAMPLE 2

Real-time Quantitative PCR Analysis of Mcl-1 mRNA Levels

Quantitation of Mcl-1 mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

Presented in Table 3 are primers and probes used to measure GAPDH expression in the cell types described herein. The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

TABLE 3

GAPDH primers and probes for use in real-time PCR

| Target Name | Species | Sequence Description | Sequence (5' to 3') | SEQ ID NO |
|---|---|---|---|---|
| GAPDH | Human | Forward Primer | CAACGGATTTGGTCGTATTGG | 24 |
| GAPDH | Human | Reverse Primer | GGCAACAATATCCACTTTACCAGAGT | 25 |
| GAPDH | Human | Probe | CGCCTGGTCACCAGGGCTGCT | 26 |
| GAPDH | Human | Forward Primer | GAAGGTGAAGGTCGGAGTC | 27 |
| GAPDH | Human | Reverse Primer | GAAGATGGTGATGGGATTTC | 28 |
| GAPDH | Human | Probe | CAAGCTTCCCGTTCTCAGCC | 29 |
| GAPDH | Human | Forward Primer | GAAGGTGAAGGTCGGAGTC | 27 |
| GAPDH | Human | Reverse Primer | GAAGATGGTGATGGGATTTC | 28 |
| GAPDH | Human | Probe | TGGAATCATATTGGAACATG | 30 |
| GAPDH | Mouse | Forward Primer | GGCAAATTCAACGGCACAGT | 31 |
| GAPDH | Mouse | Reverse Primer | GGGTCTCGCTCCTGGAAGAT | 32 |
| GAPDH | Mouse | Probe | AAGGCCGAGAATGGGAAGCTTGTCATC | 33 |
| GAPDH | Rat | Forward Primer | TGTTCTAGAGACAGCCGCATCTT | 34 |
| GAPDH | Rat | Reverse Primer | CACCGACCTTCACCATCTTGT | 35 |
| GAPDH | Rat | Probe | TTGTGCAGTGCCAGCCTCGTCTCA | 36 |

Probes and primers for use in real-time PCR were designed to hybridize to target-specific sequences. The primers and probes and Mcl-1 target nucleic acid sequences to which they hybridize are presented in Table 4. The target-specific PCR probes have FAM covalently linked to the 5' end and TAMRA or MGB covalently linked to the 3' end, where FAM is the fluorescent dye and TAMRA or MGB is the quencher dye.

TABLE 4

Mcl-1-specific primers and probes for use in real-time PCR

| Target Name | Species | Target SEQ ID NO | Sequence Description | Sequence (5' to 3') | SEQ ID NO |
|---|---|---|---|---|---|
| Mcl-1 | Human | 3 | Forward Primer | AAGATCTGGTTACGGTAACTAAAAAGC | 37 |
| Mcl-1 | Human | 3 | Reverse Primer | GGGCCCCTAAAAACCAATTC | 38 |
| Mcl-1 | Human | 3 | Probe | TGTCTGCCAAATCCAGTGGAAACAAGTG | 39 |
| Mcl-1 | Mouse | 7 | Forward Primer | TCCAGGGTGTGCTTGACAAA | 40 |
| Mcl-1 | Mouse | 7 | Reverse Primer | TCATCCAAACCAAGCCAAAGT | 41 |
| Mcl-1 | Mouse | 7 | Probe | TCCCAAGTGCTCAGGACTTTTAGCCCTG | 42 |

EXAMPLE 3

Treatment of Cultured Cells with Oligomeric Compounds

Oligomeric compounds targeted to Mcl-1 nucleic acids presented in Table 1 were tested for their effects on gene target expression in cultured cells. Table 5 shows the experimental conditions, including cell type, transfection method, dose of oligonucleotide and control SEQ ID NO used to evaluate the inhibition of gene expression by the oligomeric compounds of the invention. The control oligonucleotide was chosen from the group presented in Table 2, and in these experiments was used as a negative control. Each cell type was treated with the indicated dose of oligonucleotide as described by other examples herein. The oligomeric compounds and the data describing the degree to which they inhibit gene expression are shown in Table 6.

TABLE 5

Treatment conditions of cultured cells with oligomeric compounds

| Target Name | Cell Type | Transfection Method | Dose of Oligonucleotide (nM) | Control SEQ ID NO |
|---|---|---|---|---|
| Mcl-1 | A549 | Lipofectin | 100 | 17 |
| Mcl-1 | b.END | Cytofectin | 100 | 17 |

EXAMPLE 4

Antisense Inhibition of Gene Targets by Oligomeric Compounds

A series of oligomeric compounds was designed to target different regions of Mcl-1, using published sequences cited in Table 1. The compounds are shown in Table 6 (human) and Table 7 (mouse). All compounds in Table 6 and Table 7 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein. Data are averages from experiments in which cultured cells were treated with the disclosed oligomeric compounds. Shown in Table 6 and Table 7 is the SEQ ID NO of the sequence to which each oligomeric compound is targeted. The inhibition data presented in Table 6 and Table 7 were obtained in human A549 cells and mouse b.END cells, respectively.

A reduction in expression is expressed as percent inhibition. If the target expression level of oligomeric compound-treated cell was higher than control, percent inhibition is expressed as zero inhibition. The target regions to which these oligomeric compounds are inhibitory are herein referred to as "validated target segments."

TABLE 6

Inhibition of human Mcl-1 mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 387600 | 2 | 123 | GAGGCCAAACATTGCCAGTC | 54 | 43 |
| 387601 | 2 | 131 | TTTCTTTTGAGGCCAAACAT | 29 | 44 |
| 387602 | 2 | 573 | GGTGTTATTACCAGATTCCC | 32 | 45 |
| 387603 | 2 | 719 | CCAGACCTGCCCATTGGCTT | 67 | 46 |
| 387604 | 2 | 729 | GCTGGTGGCCCCAGACCTGC | 39 | 47 |
| 387605 | 2 | 808 | GAAGCATGCCTTGGAAGGCC | 29 | 48 |
| 387606 | 2 | 820 | TGTCCAGTTTCCGAAGCATG | 62 | 49 |
| 387607 | 2 | 873 | GAAAACATGGATCATCACTC | 33 | 50 |
| 385360 | 2 | 902 | ATCCTGCCCCAGTTTGTTAC | 48 | 51 |
| 385361 | 2 | 911 | AGAGTCACAATCCTGCCCCA | 47 | 52 |
| 387608 | 2 | 938 | TTAGCCACAAAGGCACCAAA | 47 | 53 |
| 387609 | 2 | 959 | TGGTTTATGGTCTTCAAGTG | 50 | 54 |
| 387610 | 2 | 972 | GATGCAGCTTTCTTGGTTTA | 24 | 55 |
| 387611 | 2 | 977 | GGTTCGATGCAGCTTTCTTG | 50 | 56 |
| 387612 | 2 | 988 | TTTCTGCTAATGGTTCGATG | 66 | 57 |
| 387613 | 2 | 1039 | TTTGTTTAACTAGCCAGTCC | 24 | 58 |
| 387614 | 2 | 1055 | AACCCATCCCAGCCTCTTTG | 36 | 59 |
| 387615 | 2 | 1083 | TAGGTCCTCTACATGGAAGA | 43 | 60 |
| 387616 | 2 | 1104 | CACATTCCTGATGCCACCTT | 56 | 61 |
| 387617 | 2 | 1109 | AGCAGCACATTCCTGATGCC | 43 | 62 |
| 387618 | 2 | 1131 | TCCAGCAACACCTGCAAAAG | 52 | 63 |
| 387619 | 2 | 1156 | TTAGATATGCCAAACCAGCT | 71 | 64 |
| 387620 | 2 | 1183 | TATTGCACTTACAGTAAGGC | 34 | 65 |
| 387621 | 2 | 1252 | GAAGTTACAGCTTGGAGTCC | 63 | 66 |
| 387622 | 2 | 1268 | TAGGGTGCAACTCTAGGAAG | 63 | 67 |
| 387623 | 2 | 1278 | GCTAGGTTGCTAGGGTGCAA | 67 | 68 |
| 387624 | 2 | 1319 | TATTCTTGTTAGCCATAATC | 72 | 69 |
| 387625 | 2 | 1341 | GGGAGCACTCTTCCCATGTA | 52 | 70 |
| 387626 | 2 | 1396 | GTTTGTTGCTGAAACTGAAC | 51 | 71 |
| 387627 | 2 | 1404 | CAAAGTTTGTTTGTTGCTGA | 68 | 72 |
| 387628 | 2 | 1471 | GGAAATTAAGTCTTTCCACC | 64 | 73 |
| 387629 | 2 | 1651 | GAGGAAAAGCTTCCCTTGTA | 47 | 74 |
| 387630 | 2 | 1669 | GGGAAAGCTAATTAGAGAGA | 5 | 75 |
| 387631 | 2 | 1674 | ATACTGGGAAAGCTAATTAG | 55 | 76 |
| 387632 | 2 | 1809 | ATATTCATAACTAATTACTG | 4 | 77 |

TABLE 6-continued

Inhibition of human Mcl-1 mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 387633 | 2 | 1824 | GAATTGAGGATATCCATATT | 37 | 78 |
| 387634 | 2 | 1832 | TGTCTTAAGAATTGAGGATA | 52 | 79 |
| 387635 | 2 | 1890 | TCAAAGAAATAGACTTTCTG | 58 | 80 |
| 387636 | 2 | 2062 | CTACAACCAGTCTGCATACA | 70 | 81 |
| 387637 | 2 | 2075 | CAGATTTGTTCCACTACAAC | 62 | 82 |
| 387638 | 2 | 2084 | CATAGTTATCAGATTTGTTC | 66 | 83 |
| 387639 | 2 | 2178 | GAATTTCCATTCATCAACCT | 52 | 84 |
| 387640 | 2 | 2207 | ATTGAAAACTTGCATATAAT | 32 | 85 |
| 387641 | 2 | 2248 | GTAAGTCATCAGTAACCTTA | 77 | 86 |
| 387642 | 2 | 2270 | GCCCAATCAGAGCCCATTAT | 71 | 87 |
| 387643 | 2 | 2307 | TAAATTAGGTCAAATGGAAG | 30 | 88 |
| 387644 | 2 | 2515 | AAGCCTAATAATAGCACCAT | 70 | 89 |
| 387645 | 2 | 2551 | TGACATACTAGGCTTAGACC | 62 | 90 |
| 387646 | 2 | 2566 | AAGTATTTGCTTTATTGACA | 66 | 91 |
| 387647 | 2 | 2637 | ACTGAAATCCAAAGATGCCA | 71 | 92 |
| 387648 | 2 | 2766 | AAAGAGTTCAGGGATGGCAG | 65 | 93 |
| 387649 | 2 | 2823 | GAGGGTCACTCAGGTTTCCA | 50 | 94 |
| 387650 | 2 | 2903 | ACAGCACCCATGGTATTACC | 73 | 95 |
| 387651 | 2 | 3118 | GGTTTAACACAGCTCACCTC | 73 | 96 |
| 387652 | 2 | 3126 | AACTCTGAGGTTTAACACAG | 65 | 97 |
| 387653 | 2 | 3142 | TTATCAGTAGCTTTTAAACT | 28 | 98 |
| 387654 | 2 | 3176 | TGACCCTAGTTCCAATATAG | 65 | 99 |
| 387655 | 2 | 3183 | TTTCAAATGACCCTAGTTCC | 59 | 100 |
| 387656 | 2 | 3214 | CAGACTAAAGGTCATGTTCC | 68 | 101 |
| 387657 | 2 | 3235 | CCTATTTTTAAATGGAGTCC | 70 | 102 |
| 387658 | 2 | 3388 | GGTCCTTAGAGATACATGAT | 64 | 103 |
| 387659 | 2 | 3482 | TATGCACTTGTTTCCACTGG | 92 | 104 |
| 387660 | 2 | 3579 | GCCCCAAGCCCAAAATATCA | 20 | 105 |
| 387661 | 2 | 3829 | CCCACAGAATGTACATGAAA | 63 | 106 |
| 387662 | 2 | 3902 | GTAGTTGGTCCTAACCCTTC | 63 | 107 |
| 387663 | 2 | 3940 | TAGGGAAACACACTACATTT | 26 | 108 |
| 387664 | 3 | 809 | CAAACCCATCCTTGGAAGGC | 0 | 109 |
| 385368 | 3 | 870 | GCAAAAGCCAGCAGCACATT | 49 | 110 |
| 385372 | 3 | 920 | AAGGCTATCTTATTAGATAT | 9 | 111 |
| 385421 | 3 | 2941 | TGAAGCTTTCAAATGACCCT | 53 | 112 |
| 387665 | 3 | 3428 | CAGTCAGCACTTAGACCACC | 70 | 113 |
| 387666 | 5 | 2439 | TGGCTTCAGGAATAGGATGA | 27 | 114 |
| 387667 | 5 | 2668 | GAAGCATGCCTGAGAAAGAA | 14 | 115 |
| 387668 | 5 | 2919 | AGGCAAACTTACCCAGCCTC | 22 | 116 |
| 387669 | 5 | 2996 | AAAAACCTTTAGATATCCCC | 34 | 117 |
| 387670 | 5 | 3047 | TCAAATAAACAATGGTCCTT | 62 | 118 |
| 387671 | 5 | 3176 | ATGGTTTGAATCCACTGAAG | 49 | 119 |
| 387672 | 5 | 3412 | GACTTCCAGAGTTCCCATGA | 35 | 120 |

As shown in Table 6, SEQ ID NOs 43-74, 76, 78-108, 110, 112-114 and 116-220 inhibited expression of Mcl-1 mRNA by at least 20%; SEQ ID NOs 43, 46, 49, 54, 56, 57, 61, 63, 64, 66-73, 76, 52-84, 86, 87, 89-97, 99-104, 106, 107, 112, 113 and 118 inhibited expression of Mcl-1 mRNA by at least 50%; and SEQ ID NOs 64, 69, 81, 86, 87, 89, 92, 95, 96, 102, 104 and 113 inhibited expression of Mcl-1 mRNA by at least 70%. Preferred target regions of SEQ ID NO: 2 include but are not limited to nucleotides 123-150; 719-748; 808-839; 902-930; 902-1007; 938-1007; 1039-1074; 1083-1150; 1104-1128; 1252-1297; 1396-1423; 1651-1693; 1809-1851; 2062-2103; 2551-2585; 3118-3161; 3176-3202; and 3214-3254, and any range therewithin.

TABLE 7

Inhibition of mouse Mcl-1 mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 385358 | 7 | 763 | TTGAAAACATGGACCATTAC | 75 | 121 |
| 385359 | 7 | 769 | CCATCTTTGAAAACATGGAC | 60 | 122 |
| 385360 | 7 | 790 | ATCCTGCCCCAGTTTGTTAC | 70 | 51 |
| 385361 | 7 | 799 | AGAGTCACAATCCTGCCCCA | 67 | 52 |
| 385362 | 7 | 805 | GAAATAAGAGTCACAATCCT | 28 | 123 |
| 385363 | 7 | 829 | TGTTTGGCCACAAAGGCACC | 45 | 124 |
| 385364 | 7 | 837 | TCTTTAAGTGTTTGGCCACA | 61 | 125 |
| 385365 | 7 | 881 | GATAGTTTCTGCTAATGGTT | 59 | 126 |
| 385366 | 7 | 927 | TTTGTTTGACAAGCCAGTCC | 55 | 127 |
| 385367 | 7 | 997 | AGCAGCACATTTCTGATGCC | 55 | 128 |
| 385368 | 7 | 1006 | GCAAAAGCCAGCAGCACATT | 60 | 110 |
| 385369 | 7 | 1038 | ATGCCAGACCAGCCCCTACT | 69 | 129 |

TABLE 7-continued

Inhibition of mouse Mcl-1 mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 385370 | 7 | 1043 | TAGATATGCCAGACCAGCCC | 69 | 130 |
| 385371 | 7 | 1048 | CTTATTAGATATGCCAGACC | 57 | 131 |
| 385372 | 7 | 1056 | AAGGCTATCTTATTAGATAT | 38 | 111 |
| 385373 | 7 | 1060 | TCACAAGGCTATCTTATTAG | 65 | 132 |
| 385374 | 7 | 1099 | TAGTTTGGTGGCTGGAGCTT | 59 | 133 |
| 385375 | 7 | 1115 | TTTTCACAGATGCATGTAGT | 71 | 134 |
| 385376 | 7 | 1130 | TCATAAATACACATGTTTTC | 43 | 135 |
| 385377 | 7 | 1156 | AATCCTGGGCAGCTTCAAGT | 80 | 136 |
| 385378 | 7 | 1274 | TCATTCAGACAGTGACTCTT | 70 | 137 |
| 385379 | 7 | 1279 | TTGCTTCATTCAGACAGTGA | 71 | 138 |
| 385380 | 7 | 1284 | GAACTTTGCTTCATTCAGAC | 71 | 139 |
| 385381 | 7 | 1335 | TCATTCATTCTAGAAGTCCT | 65 | 140 |
| 385382 | 7 | 1415 | TATTGAGCTTTGTGACTAGC | 87 | 141 |
| 385383 | 7 | 1434 | GAGCAGAGTAATGGATATTT | 77 | 142 |
| 385384 | 7 | 1443 | CAACACTCTGAGCAGAGTAA | 74 | 143 |
| 385385 | 7 | 1488 | CCATTTTACACAAGTCACCA | 45 | 144 |
| 385386 | 7 | 1500 | TAGGTTACAAATCCATTTTA | 51 | 145 |
| 385387 | 7 | 1506 | GACTTGTAGGTTACAAATCC | 36 | 146 |
| 385388 | 7 | 1598 | GCACTTGGGACTTTGTCAAG | 79 | 147 |
| 385389 | 7 | 1610 | TAAAAGTCCTGAGCACTTGG | 65 | 148 |
| 385390 | 7 | 1620 | TAGACAGGGCTAAAAGTCCT | 58 | 149 |
| 385391 | 7 | 1630 | CAAGCCAAAGTAGACAGGGC | 85 | 150 |
| 385392 | 7 | 1671 | TTGGCCATCACTAGGCTAAT | 85 | 151 |
| 385393 | 7 | 1700 | TAATTAGTGAACCTTAAGTC | 69 | 152 |
| 385394 | 7 | 1711 | AGTTTTGTAACTAATTAGTG | 45 | 153 |
| 385395 | 7 | 1758 | TACAGACAAATACATTTCAT | 53 | 154 |
| 385396 | 7 | 1763 | ATTTTTACAGACAAATACAT | 19 | 155 |
| 385397 | 7 | 1769 | TATACAATTTTTACAGACAA | 33 | 156 |
| 385398 | 7 | 1800 | TGTTCAAAGAAATAGACTTT | 53 | 157 |
| 385399 | 7 | 1850 | CAAATTTCAAAAGGGTATGG | 63 | 158 |
| 385400 | 7 | 1873 | TACATTTCTAACTAGAGAAG | 22 | 159 |
| 385401 | 7 | 1878 | AGAAATACATTTCTAACTAG | 21 | 160 |
| 385402 | 7 | 1935 | CACACAACAGGCTCTGCATA | 75 | 161 |
| 385403 | 7 | 1947 | AACCAGTCCACACACACAAC | 71 | 162 |
| 385404 | 7 | 1955 | AAATCTATAACCAGTCCACA | 65 | 163 |
| 385405 | 7 | 2035 | GATCAAATGTCTTACATCTA | 72 | 164 |
| 385406 | 7 | 2055 | AATTTTGTAAGTCAACAGGG | 75 | 165 |
| 385407 | 7 | 2095 | TAGCACCATGGTTAAGACTC | 77 | 166 |
| 385408 | 7 | 2124 | ACTTGTGTTAAACAAGTAAA | 23 | 167 |
| 385409 | 7 | 2146 | GTTTTATTGACACCAGGTAT | 69 | 168 |
| 385410 | 7 | 2149 | TTTGTTTTATTGACACCAGG | 67 | 169 |
| 385411 | 7 | 2161 | AAGAAATACATATTTGTTTT | 25 | 170 |
| 385412 | 7 | 2178 | GGCAATCCTTAGTAGACAAG | 84 | 171 |
| 385413 | 7 | 2234 | GTAAAGGAAGTAAAGGCTAC | 61 | 172 |
| 385414 | 7 | 2295 | AGAGCACAGGGAGGAAGTGT | 58 | 173 |
| 385415 | 7 | 2302 | CCAGTGAAGAGCACAGGGAG | 74 | 174 |
| 385416 | 7 | 2472 | CCAAGAATGCCAATCCCTGG | 76 | 175 |
| 385417 | 7 | 2552 | CCAACCTTTGAAATTCCCAA | 75 | 176 |
| 385418 | 7 | 2593 | CATACTTGGAGCAAACTAAT | 53 | 177 |
| 385419 | 7 | 2611 | AACTTAAGTGAACACAGTCA | 60 | 178 |
| 385420 | 7 | 2665 | TCAGTTACCAGTGGCTTTTG | 71 | 179 |
| 385421 | 7 | 2698 | TGAAGCTTTCAAATGACCCT | 69 | 112 |
| 385422 | 7 | 2724 | CCTGACTAAAGGTCACATTC | 46 | 180 |
| 385423 | 7 | 2799 | CCAAGCTGGCAGGCAGGGCA | 78 | 181 |
| 385424 | 7 | 3055 | CCAAGTCTTCATGGCCCTGG | 73 | 182 |
| 385425 | 7 | 3127 | ATTCATCTAGTCAGCACTCA | 66 | 183 |
| 385426 | 7 | 3283 | TACCAGAATGAAGGTGTTCA | 53 | 184 |
| 385427 | 7 | 3290 | GGTGCTCTACCAGAATGAAG | 66 | 185 |
| 385428 | 7 | 3345 | CCACATTAACTTGCAGTTGG | 71 | 186 |
| 385429 | 9 | 2764 | TCTAGAGCAGTCAGGCAGAC | 46 | 187 |
| 385430 | 9 | 2869 | GGAGCATGCCTGAGAAGAAA | 66 | 188 |
| 385431 | 9 | 3166 | CAAAATCCTGCACCCCATTT | 55 | 189 |
| 385432 | 9 | 3358 | AGATTATCCAACTGAATTAG | 49 | 190 |
| 385433 | 9 | 3491 | GAGCTGGTGTATTTGGGTAT | 56 | 191 |
| 385434 | 9 | 3587 | TGAGCAGGGCCCATAACCAA | 73 | 192 |
| 385435 | 9 | 3784 | ACATTTTCAAGTATGGGTTT | 43 | 193 |

As shown in Table 7, SEQ ID NOs 51, 52, 110, 112, 121, 122, 124-145, 147, 148, 150-154, 157, 158, 161-166, 168, 169 and 171-193 inhibited expression of Mcl-1 mRNA by at least 40%; SEQ ID NOs 51, 52, 110, 112, 121, 122, 125, 129, 130, 132, 134, 136-143, 147, 148, 150-152, 158, 161-166, 168, 169 and 171, 172, 174-176, 178, 179, 181-183, 185, 186, 188 and 192 inhibited expression of Mcl-1 mRNA by at least 60%; and SEQ ID NOs 136, 141, 150, 151 and 171 inhibited expression of Mcl-1 mRNA by at least 80%. Preferred target regions of SEQ ID NO: 7 include but are not limited to nucleobases 763-856; 763-824; 763-788; 790-856; 790-824; 829-856; 997-1025; 1038-1079; 1099-1149; 1274-1303; 1415-1462; 1488-1525; 1598-1649; 1700-1730; 1758-1788; 1873-1897; 1935-1974; 2146-2197; 2295-2321; 2593-2630; and 3283-3319, and any range therewithin.

What is claimed is:

1. A compound comprising a modified oligonucleotide consisting of 12 to 30 linked nucleosides and having a nucleobase sequence comprising at least 8 consecutive nucleobases of a nucleobase sequence selected from the group consisting of SEQ ID NO: 86 and 87, and wherein the nucleobase sequence of the modified oligonucleotide is at least 90% complementary to a nucleic acid molecule encoding human Mcl-1 having SEQ ID NO: 2 as measured over the entirety of said modified oligonucleotide nucleobase sequence.

2. The compound of claim 1, consisting of a single-stranded modified oligonucleotide.

3. The compound of claim 2, wherein the nucleobase sequence of the modified oligonucleotide is 100% complementary to a nucleic acid molecule encoding human Mcl-1 having SEQ ID NO: 2 as measured over the entirety of said modified oligonucleotide nucleobase sequence.

4. The compound of claim 2, wherein at least one internucleoside linkage is a modified internucleoside linkage.

5. The compound of claim 4, wherein each internucleoside linkage is a phosphorothioate internucleoside linkage.

6. The compound of claim 2, wherein at least one nucleoside comprises a modified sugar.

7. The compound of claim 6, wherein at least one modified sugar is a bicyclic sugar.

8. The compound of claim 6, wherein at least one modified sugar is selected from the group consisting of a 2'-O-(2-methoxyethyl), and a 4'-$(CH_2)_n$—O-2' bridge, wherein n is 1 or 2.

9. The compound of claim 2, wherein at least one nucleoside comprises a modified nucleobase.

10. The compound of claim 9, wherein the modified nucleobase is a 5-methylcytosine.

11. The compound of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

12. The compound of claim 11, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein each cytidine residue in said modified oligonucleotide is a 5-methylcytidine residue, and wherein each internucleoside linkage of said modified oligonucleotide is a phosphorothioate linkage.

13. The compound of claim 12, wherein the modified oligonucleotide consists of 20 linked nucleosides.

14. The compound of claim 13, wherein said modified oligonucleotide consists of SEQ ID NO: 86.

15. The compound of claim 13, wherein said modified oligonucleotide consists of SEQ ID NO: 87.

16. A composition comprising the compound of claim 1, or a salt thereof, and a pharmaceutically acceptable carrier or diluent.

17. The composition of claim 16, wherein said compound consists of a single-stranded oligonucleotide.

18. The composition of claim 16, wherein the modified oligonucleotide consists of 20 linked nucleosides.

19. A method of modulating expression of Mcl-1 in a cell, tissue or animal, comprising administering to said cell, tissue or animal the compound of claim 1 in an amount sufficient to modulate expression of Mcl-1.

20. A method of inducing apoptosis of a cell, comprising administering to said cell the compound of claim 1 in an amount sufficient to induce apoptosis of said cell.

21. A method of inhibiting proliferation of a cell, comprising administering to said cell the compound of claim 1 in an amount sufficient to inhibit proliferation of said cell.

* * * * *

SEQUENCE LISTING

<160> NUMBER OF SEQ ID NOS: 193

<210> SEQ ID NO 1
<211> LENGTH: 3934
<212> TYPE: DNA
<213> ORGANISM: Homo sapiens

<400> SEQUENCE: 1

```
tccagtaagg agtcggggtc ttccccagtt ttctcagcca ggcggcggcg gcgactggca      60
atgtttggcc tcaaaagaaa cgcggtaatc ggactcaacc tctactgtgg ggggccggc     120
ttgggggccg gcagcggcgg cgccacccgc ccgggagggc gacttttggc tacgagaag     180
gaggcctcgg cccggcgaga gataggggga ggggaggccg gcgcggtgat ggcggaagc     240
gccggcgcaa gcccccgtc cacccctcacg ccagactccc ggagggtcgc gcggccgccg    300
cccattggcg ccgaggtccc cgacgtcacc gcgaccccg cgaggctgct tttcttcgcg     360
cccacccgcc gcgcggcgcc gcttgaggag atggaagccc cggccgctga cgccatcatg    420
tcgcccgaag aggagctgga cgggtacgag ccggagcctc tcgggaagcg gccggctgtc    480
ctgccgctgc tggagttggt cggggaatct ggtaataaca ccagtacgga cgggtcacta    540
ccctcgacgc cgccgccagc agaggaggag gaggacgagt tgtaccggca gtcgctggag    600
attatctctc ggtaccttcg ggagcaggcc accggcgcca aggacacaaa gccaatgggc    660
aggtctgggg ccaccagcag gaaggcgctg gagaccttac gacgggttgg ggatggcgtg    720
cagcgcaacc acgagacggt cttccaaggc atgcttcgga aactggacat caaaaacgaa    780
gacgatgtga atcgttgtc tcgagtgatg atccatgttt tcagcgacgg cgtaacaaac    840
tggggcagga ttgtgactct catttctttt ggtgcctttg tggctaaaca cttgaagacc    900
ataaaccaag aaagctgcat cgaaccatta gcagaaagta tcacagacgt tctcgtaagg    960
acaaaacggg actggctagt taaacaaaga ggctgggatg ggtttgtgga gttcttccat   1020
gtagaggacc tagaaggtgg catcaggaat gtgctgctgg cttttgcagg tgttgctgga   1080
gtaggagctg gtttggcata tctaataaga tagccttact gtaagtgcaa tagttgactt   1140
ttaaccaacc accaccacca ccaaaaccag tttatgcagt tggactccaa gctgtaactt   1200
cctagagttg caccctagca acctagccag aaaagcaagt ggcaagagga ttatggctaa   1260
caagaataaa tacatgggaa gagtgctccc cattgattga agagtcactg tctgaaagaa   1320
gcaaagttca gtttcagcaa caaacaaact tgtttggga agctatggag gaggacttt      1380
agatttagtg aagatggtag ggtggaaaga cttaatttcc ttgttgagaa caggaaagtg   1440
gccagtagcc aggcaagtca tagaattgat tacccgccga attcattaat ttactgtagt   1500
agtgttaaga gaagcactaa gaatgccagt gacctgtgta aaagttacaa gtaatagaac   1560
tatgactgta agcctcagta ctgtacaagg gaagcttttc ctctctctaa ttagctttcc   1620
cagtatactt cttagaaagt ccaagtgttc aggactttta tacctgttat actttggctt   1680
ggttccatga ttcttacttt attagcctag tttatcacca ataatacttg acggaaggct   1740
```

-continued

| | |
|---|---|
| cagtaattag ttatgaatat ggatatcctc aattcttaag acagcttgta aatgtatttg | 1800 |
| taaaaattgt atatatttt acagaaagtc tatttccttg aaacgaagga agtatcgaat | 1860 |
| ttacattagt tttttcata ccctttgaa ctttgcaact tccgtaatta ggaacctgtt | 1920 |
| tcttacagct tttctatgct aaactttgtt ctgttcagtt ctagagtgta tacagaacga | 1980 |
| attgatgtgt aactgtatgc agactggttg tagtggaaca atctgataa ctatgcaggt | 2040 |
| ttaaattttc ttatctgatt ttggtaagta ttccttagat aggttttctt tgaaaacctg | 2100 |
| ggattgagag gttgatgaat ggaaattctt tcacttcatt atatgcaagt tttcaataat | 2160 |
| taggtctaag tggagtttta aggttactga tgacttacaa ataatgggct ctgattgggc | 2220 |
| aatactcatt tgagttcctt ccatttgacc taatttaact ggtgaaattt aaagtgaatt | 2280 |
| catgggctca tctttaaagc ttttactaaa agattttcag ctgaatggaa ctcattagct | 2340 |
| gtgtgcatat aaaagatca catcaggtgg atggagagac atttgatccc ttgtttgctt | 2400 |
| aataaattat aaaatgatgg cttggaaaag caggctagtc taaccatggt gctattatta | 2460 |
| ggcttgcttg ttacacacac aggtctaagc ctagtatgtc aataaagcaa atacttactg | 2520 |
| ttttgtttct attaatgatt cccaaaacctt gttgcaagtt tttgcattgg catctttgga | 2580 |
| tttcagtctt gatgtttgtt ctatcagact taacctttta tttcctgtcc ttccttgaaa | 2640 |
| ttgctgattg ttctgctccc tctacagata tttatatcaa ttcctacagc tttcccctgc | 2700 |
| catccctgaa ctcttctag ccctttaga ttttggcact gtgaaacccc tgctggaaac | 2760 |
| ctgagtgacc ctcccctcccc accaagagtc cacagacctt tcatctttca cgaacttgat | 2820 |
| cctgttagca ggtggtaata ccatgggtgc tgtgacacta acagtcattg agaggtggga | 2880 |
| ggaagtccct tttccttgga ctggtatctt ttcaactatt gttttatcct gtctttgggg | 2940 |
| gcaatgtgtc aaaagtcccc tcaggaattt tcagaggaaa gaacatttta tgaggctttc | 3000 |
| tctaaagttt cctttgtata ggagtatgct cacttaaatt tacagaaaga ggtgagctgt | 3060 |
| gttaaacctc agagtttaaa agctactgat aaactgaaga aagtgtctat attggaacta | 3120 |
| gggtcatttg aaagcttcag tctcggaaca tgacctttag tctgtggact ccatttaaaa | 3180 |
| ataggtatga ataagatgac taagaatgta atggggaaga actgccctgc ctgcccatct | 3240 |
| cagagccata aggtcatctt tgctagagct attttacct atgtatttat cgttcttgat | 3300 |
| cataagccgc ttatttatat catgtatctc taaggaccta aaagcacttt atgtagtttt | 3360 |
| taattaatct taagatctgg ttacggtaac taaaagcctg tctgccaaat ccagtggaaa | 3420 |
| caagtgcata gatgtgaatt ggttttagg ggccccactt cccaattcat taggtatgac | 3480 |
| tgtggaaata cagacaagga cttagttgat attttgggct tggggcagtg agggcttagg | 3540 |
| acaccccaag tggtttggga aaggaggagg gagtggtggg tttataggg aggaggaggc | 3600 |
| aggtggtcta agtgctgact ggctacgtag ttcgggcaaa tcctccaaaa gggaaaggga | 3660 |
| ggatttgctt agaaggatgg ggctcccagt gactacttt tgacttctgt ttgtcttacg | 3720 |
| cttctctcag ggaaaaacat gcagtcctct agtgtttcat gtacattctg tgggggtga | 3780 |
| acaccttggt tctggttaaa cagctgtact tttgatagct gtgccaggaa gggttaggac | 3840 |
| caactacaaa ttaatgttgg ttgtcaaatg tagtgtgttt ccctaacttt ctgttttcc | 3900 |
| tgagaaaaaa aaataaatct tttattcaaa taaa | 3934 |

<210> SEQ ID NO 2
<211> LENGTH: 4020
<212> TYPE: DNA
<213> ORGANISM: Homo sapiens

<400> SEQUENCE: 2

```
caccccgtag gactggccgc cctaaaaccg tgataaagga gctgctcgcc acttctcact      60
tccgcttcct tccagtaagg agtcggggtc ttccccagtt ttctcagcca ggcggcggcg     120
gcgactggca atgtttggcc tcaaaagaaa cgcggtaatc ggactcaacc tctactgtgg     180
gggggccggc ttggggccg gcagcggcgg cgccacccgc ccgggagggc gacttttggc      240
tacggagaag gaggcctcgg cccggcgaga gataggggga ggggaggccg gcgcggtgat     300
tggcggaagc gccggcgcaa gccccccgtc caccctcacg ccagactccc ggagggtcgc     360
gcggccgccg cccattggcg ccgaggtccc cgacgtcacc gcgaccccg cgaggctgct      420
tttcttcgcg cccacccgcc gcgcggcgcc gcttgaggag atggaagccc cggccgctga    480
cgccatcatg tcgcccgaag aggagctgga cgggtacgag ccggagcctc tcgggaagcg    540
gccggctgtc ctgccgctgc tggagttggt cggggaatct ggtaataaca ccagtacgga    600
cgggtcacta ccctcgacgc cgccgccagc agaggaggag gaggacgagt tgtaccggca    660
gtcgctggag attatctctc ggtaccttcg ggagcaggcc accggcgcca aggacacaaa    720
gccaatgggc aggtctgggg ccaccagcag gaaggcgctg gagaccttac gacgggttgg    780
ggatggcgtg cagcgcaacc acgagacggc cttccaaggc atgcttcgga aactggacat    840
caaaaacgaa gacgatgtga atcgttgtc tcgagtgatg atccatgttt tcagcgacgg     900
cgtaacaaac tggggcagga ttgtgactct catttctttt ggtgcctttg tggctaaaca    960
cttgaagacc ataaaccaag aaagctgcat cgaaccatta gcagaaagta tcacagacgt   1020
tctcgtaagg acaaaacggg actggctagt taaacaaaga ggctgggatg ggtttgtgga   1080
gttcttccat gtagaggacc tagaaggtgg catcaggaat gtgctgctgg cttttgcagg   1140
tgttgctgga gtaggagctg gtttggcata tctaataaga tagccttact gtaagtgcaa   1200
tagttgactt ttaaccaacc accaccacca ccaaaaccag tttatgcagt tggactccaa   1260
gctgtaactt cctagagttg caccctagca acctagccag aaaagcaagt ggcaagagga   1320
ttatggctaa caagaataaa tacatgggaa gagtgctccc cattgattga agagtcactg   1380
tctgaaagaa gcaaagttca gtttcagcaa caaacaaact ttgtttggga agctatggag   1440
gaggacttt agatttagtg aagatggtag ggtggaaaga cttaatttcc ttgttgagaa    1500
caggaaagtg gccagtagcc aggcaagtca tagaattgat tacccgccga attcattaat   1560
ttactgtagt gttaagagaa gcactaagaa tgccagtgac ctgtgtaaaa gttacaagta   1620
atagaactat gactgtaagc ctcagtactg tacaagggaa gcttttcctc tctctaatta   1680
gctttcccag tatacttctt agaaagtcca agtgttcagg actttatac ctgttatact    1740
ttggcttggt ttccatgatt cttactttat tagcctagtt tatcaccaat aatacttgac   1800
ggaaggctca gtaattagtt atgaatatgg atatcctcaa ttcttaagac agcttgtaaa   1860
tgtatttgta aaaattgtat atattttac agaaagtcta tttctttgaa acgaaggaag    1920
tatcgaattt acattagttt ttttcatacc cttttgaact ttgcaacttc cgtaattagg   1980
aacctgtttc ttacagcttt tctatgctaa actttgttct gttcagttct agagtgtata   2040
cagaacgaat tgatgtgtaa ctgtatgcag actggttgta gtggaacaaa tctgataact   2100
atgcaggttt aaattttctt atctgatttt ggtaagtatt ccttagatag gttttcttt    2160
gaaaacctgg gattgagagg ttgatgaatg gaaattcttt cacttcatta tatgcaagtt   2220
ttcaataatt aggtctaagt ggagttttaa ggttactgat gacttacaaa taatgggctc   2280
```

```
tgattgggca atactcattt gagttccttc catttgacct aatttaactg gtgaaattta    2340
aagtgaattc atgggctcat ctttaaagct tttactaaaa gattttcagc tgaatggaac    2400
tcattagctg tgtgcatata aaagatcac atcaggtgga tggagagaca tttgatccct    2460
tgtttgctta ataaattata aaatgatggc ttggaaaagc aggctagtct aaccatggtg    2520
ctattattag gcttgcttgt tacacacaca ggtctaagcc tagtatgtca ataaagcaaa    2580
tacttactgt tttgtttcta ttaatgattc ccaaaccttg ttgcaagttt ttgcattggc    2640
atctttggat ttcagtcttg atgtttgttc tatcagactt aaccttttat ttcctgtcct    2700
tccttgaaat tgctgattgt tctgctccct ctacagatat ttatatcaat tcctacagct    2760
ttcccctgcc atccctgaac tcttttctagc cctttttagat tttggcactg tgaaacccct    2820
gctgaaaacc tgagtgaccc tccctcccca ccaagagtcc acagaccttt catctttcac    2880
gaacttgatc ctgttagcag gtggtaatac catgggtgct gtgacactaa cagtcattga    2940
gaggtgggag gaagtccctt ttccttggac tggtatcttt tcaactattg ttttatcctg    3000 tctttgggg caatgtgtca aaagtcccct caggaatttt cagaggaaag aacatttttat    3060 gaggctttct ctaaagtttc ctttgtatag gagtatgctc acttaaattt acagaaagag    3120
gtgagctgtg ttaaacctca gagtttaaaa gctactgata aactgaagaa agtgtctata    3180
ttggaactag ggtcatttga aagcttcagt ctcggaacat gacctttagt ctgtggactc    3240
catttaaaaa taggtatgaa taagatgact aagaatgtaa tgggggaagaa ctgccctgcc    3300 tgcccatctc agagccataa ggtcatcttt gctagagcta ttttttaccta tgtatttatc    3360 gttcttgatc ataagccgct tatttatatc atgtatctct aaggacctaa aagcacttta    3420
tgtagttttt aattaatctt aagatctggt tacggtaact aaaaaagcct gtctgccaaa    3480
tccagtggaa acaagtgcat agatgtgaat tggttttag gggcccact tcccaattca    3540 ttaggtatga ctgtggaaat acagacaagg atcttagttg atattttggg cttggggcag    3600
tgagggctta ggacacccca agtggtttgg gaaaggagga ggggagtggt gggtttatag    3660
ggggaggagg aggcaggtgg tctaagtgct gactggctac gtagttcggg caaatcctcc    3720
aaaagggaaa gggaggattt gcttagaagg atggcgctcc cagtgactac ttttttgactt    3780 ctgtttgtct tacgcttctc tcagggaaaa acatgcagtc ctctagtgtt tcatgtacat    3840
tctgtggggg gtgaacacct tggttctggt taaacagctg tacttttgat agctgtgcca    3900
ggaagggtta ggaccaacta caaattaatg ttggttgtca aatgtagtgt gtttccctaa    3960 cttttctgttt ttcctgagaa aaaaaaataa atctttttatt caaaaaaaaa aaaaaaaaa    4020

<210> SEQ ID NO 3
<211> LENGTH: 3772
<212> TYPE: DNA
<213> ORGANISM: Homo sapiens

<400> SEQUENCE: 3
caccccgtag gactggccgc cctaaaaccg tgataaagga gctgctcgcc acttctcact     60
tccgcttcct tccagtaagg agtcgggtc ttccccagtt ttctcagcca ggcggcggcg    120
gcgactggca atgtttggcc tcaaaagaaa cgcggtaatc ggactcaacc tctactgtgg    180
gggggccggt ttgggggccg gcagcggcgg cgccacccgc ccgggagggc gacttttggc    240
tacggagaag gaggcctcgg cccggcgaga gatagggga gggaggccg gcgcggtgat    300 tggcggaagc gccggcgcaa gccccccgtc caccctcacg ccagactccc ggagggtcgc    360
gcggccgccg cccattggcg ccgaggtccc cgacgtcacc gcgacccccg cgaggctgct    420
```

-continued

```
tttcttcgcg cccacccgcc gcgcggcgcc gcttgaggag atggaagccc cggccgctga    480
cgccatcatg tcgcccgaag aggagctgga cgggtacgag ccggagcctc tcgggaagcg    540
gccggctgtc ctgccgctgc tggagttggt cggggaatct ggtaataaca ccagtacgga    600
cgggtcacta ccctcgacgc cgccgccagc agaggaggag gaggacgagt tgtaccggca    660
gtcgctggag attatctctc ggtaccttcg ggagcaggcc accggcgcca aggacacaaa    720
gccaatgggc aggtctgggg ccaccagcag gaaggcgctg gagaccttac gacgggttgg    780
ggatggcgtg cagcgcaacc acgagacggc cttccaagga tgggtttgtg gagttcttcc    840
atgtagagga cctagaaggt ggcatcagga atgtgctgct ggcttttgca ggtgttgctg    900
gagtaggagc tggtttggca tatctaataa gatagcctta ctgtaagtgc aatagttgac    960
ttttaaccaa ccaccaccac caccaaaacc agtttatgca gttggactcc aagctgtaac   1020
ttcctagagt tgcaccctag caacctagcc agaaaagcaa gtggcaagag gattatggct   1080
aacaagaata aatacatggg aagagtgctc cccattgatt gaagagtcac tgtctgaaag   1140
aagcaaagtt cagtttcagc aacaaacaaa cttgtttgg gaagctatgg aggaggactt   1200
ttagatttag tgaagatggt agggtggaaa gacttaattt ccttgttgag aacaggaaag   1260
tggccagtag ccaggcaagt catagaattg attacccgcc gaattcatta atttactgta   1320
gtgttaagag aagcactaag aatgccagtg acctgtgtaa aagttacaag taatagaact   1380
atgactgtaa gcctcagtac tgtacaaggg aagcttttcc tctctctaat tagctttccc   1440
agtatacttc ttagaaagtc caagtgttca ggactttat acctgttata ctttggcttg   1500
gtttccatga ttcttacttt attagcctag tttatcacca ataatacttg acggaaggct   1560
cagtaattag ttatgaatat ggatatcctc aattcttaag acagcttgta aatgtatttg   1620
taaaaattgt atatatttt acagaaagtc tatttctttg aaacgaagga agtatcgaat   1680
ttacattagt ttttttcata ccctttttgaa ctttgcaact tccgtaatta ggaacctgtt   1740
tcttacagct tttctatgct aaactttgtt ctgttcagtt ctagagtgta tacagaacga   1800
attgatgtgt aactgtatgc agactggttg tagtggaaca aatctgataa ctatgcaggt   1860
ttaaattttc ttatctgatt ttggtaagta ttccttagat aggttttct ttgaaaacct   1920 gggattgaga ggttgatgaa tgaaattct ttcacttcat tatatgcaag ttttcaataa   1980
ttaggtctaa gtggagtttt aaggttactg atgacttaca aataatgggc tctgattggg   2040
caatactcat ttgagttcct tccatttgac ctaatttaac tggtgaaatt taaagtgaat   2100
tcatgggctc atcttaaag cttttactaa aagatttca gctgaatgga actcattagc   2160
tgtgtgcata taaaaagatc acatcaggtg gatggagaga catttgatcc cttgtttgct   2220
taataaatta taaaatgatg gcttggaaaa gcaggctagt ctaaccatgg tgctattatt   2280
aggcttgctt gttacacaca caggtctaag cctagtatgt caataaagca aatacttact   2340
gttttgtttc tattaatgat tcccaaacct tgttgcaagt ttttgcattg gcatctttgg   2400
atttcagtct tgatgtttgt tctatcagac ttaaccttt atttcctgtc ttccttgaa   2460 attgctgatt gttctgctcc ctctacagat atttatatca attcctacag cttccctg    2520 ccatccctga actctttcta gcccttttag attttggcac tgtgaaaccc ctgctggaaa   2580
cctgagtgac cctcctccc caccaagagt ccacagacct tcatctttc acgaacttga   2640 tcctgttagc aggtggtaat accatgggtg ctgtgacact aacagtcatt gagaggtggg   2700
aggaagtccc ttttccttgg actggtatct tttcaactat tgttttatcc tgtctttggg   2760
```

```
ggcaatgtgt caaaagtccc ctcaggaatt ttcagaggaa agaacatttt atgaggcttt    2820
ctctaaagtt tcctttgtat aggagtatgc tcacttaaat ttacagaaag aggtgagctg    2880
tgttaaacct cagagtttaa aagctactga taaactgaag aaagtgtcta tattggaact    2940
agggtcattt gaaagcttca gtctcggaac atgaccttta gtctgtggac tccatttaaa    3000
aataggtatg aataagatga ctaagaatgt aatggggaag aactgccctg cctgcccatc    3060
tcagagccat aaggtcatct ttgctagagc tattttttacc tatgtattta tcgttcttga    3120
tcataagccg cttatttata tcatgtatct ctaaggacct aaaagcactt tatgtagttt    3180
ttaattaatc ttaagatctg gttacggtaa ctaaaaaagc ctgtctgcca aatccagtgg    3240
aaacaagtgc atagatgtga attggttttt aggggcccca cttcccaatt cattaggtat    3300
gactgtggaa atacagacaa ggatcttagt tgatattttg ggcttggggc agtgagggct    3360
taggacaccc caagtggttt gggaaaggag gaggggagtg gtgggtttat aggggaggaa    3420
ggaggcaggt ggtctaagtg ctgactggct acgtagttcg ggcaaatcct ccaaaaggga    3480
aagggaggat ttgcttagaa ggatggcgct cccagtgact acttttttgac ttctgtttgt    3540 cttacgcttc tctcagggaa aaacatgcag tcctctagtg tttcatgtac attctgtggg    3600
gggtgaacac cttggttctg gttaaacagc tgtacttttg atagctgtgc caggaagggt    3660
taggaccaac tacaaattaa tgttggttgt caaatgtagt gtgtttccct aactttctgt    3720
ttttcctgag aaaaaaaaat aaatcttta ttcaaaaaaa aaaaaaaaa aa              3772

<210> SEQ ID NO 4
<211> LENGTH: 506
<212> TYPE: DNA
<213> ORGANISM: Homo sapiens

<400> SEQUENCE: 4
ccggcaccgg caccggcccc ggcccgcccc cggcccggcc gggcagctgg taggtgccgt      60
gcgcaaccct ccggaagctg ccgcccctttt cccctttttat gggaatactt ttttttaaaaa    120 aaaagagttc gctggcgcca ccccgtagga ctggccgccc taaaaccgtg ataaaggagc     180
tgctcgccac ttctcacttc cgcttccttc cagtaaggag tcgggtcttt ccccagtttt     240
ctcagccagg cggcggcggc gactggcaat gtttggcctc aaaagaaacg cggtaatcgg    300
actcaacctc tactgtgggg gggccggctt ggggccggag agcggcggcg ccacccgccc    360 ggagggcga cttttggcta cggagaagga ggcctcggcc cggcgagaga taggggaggg    420
ggaggccggc gcggtgattg gcggaagcgc cggcgcaagc cccccgtcca ccctcacgcc    480
agactcccgg agggtcgcgc ggccgc                                        506

<210> SEQ ID NO 5
<211> LENGTH: 8001
<212> TYPE: DNA
<213> ORGANISM: Homo sapiens

<400> SEQUENCE: 5
gatcacctga ggccaggagt ttgagaccag cctggccaac atggtgaaac cacattgtca      60
ggcctctgag cccaagccaa gccatcgcat cccctgtgac ttgcacgtat acatccagat     120
ggcctgaagt aactgaagat ccacaaaaga agtaaaaata gccttaactg atgacattcc     180
accattgtga tttgtttctg ccccacccga actgatcaat gtactttgta atctccccca     240
cccttaagaa ggttctttgt aattctcccc acccttgaga atgtactttg tgagatccac     300
ccctgcccac aaaacattgc tctcaacttc accacctatc ccaaaacctg taagaactaa     360
```

```
tgataatcca tcacccttg ctgactctct tttcggactc agcccgcctg cacccaggtg    420
aaataaacag ccatgttgct cacacaaagc ctgtttggtg gtgtcttcac acagacgcgc    480
atgaaacaca tctctactaa aaatacaata atcagctggg cgaggtggct cacagctgta    540
atctcagcac tttgggaggc cgagacaggc aggtcacttg aggccatgag ttcgagacca    600
gcctggccaa catcgtgaaa accccatctc taccaaaaat acaaaaacta gccagatgtg    660
gtggcgcacg cctgtaatcc cagctactcg ggaggctgag gtaccgaatc gtctgaacgt    720
gggaagtgga gcttgtagtg agccgagatc gccccactgc actccagcct gggcaacaga    780
gctagactgt ctcaaaacaa acaaaaaatg gtgtcaagac tctcagacga gattctaatg    840
gattaaggcc tatatgtaaa tagcaccaaa gactatggaa cagagatggg agaagcaagc    900
agggaggcag gaatagttta gctgtggcag ttttagctta gtccacttac ataaatggtt    960
ctttagggta gcacgtggag catcctcatt tccaaacatt ggactgagag tagagagctg   1020
tgcaaaataa ccacaagtcc ccaactatgc cctcttaatt atccctatca tctaagactg   1080
ttgttcccat ccatcactga acttccccgt cctcttcctt caaccctgt gttagtcaat    1140 ggttgaaatt ttgatttggt aaaaaacctc tggcgaaaac cagcaaaaag ggctcacaaa   1200
tcaggtctca gggaagcaca gaggtagcca cgagaaggcc cgaggtgctc atggaaagag   1260
ctcgagccca ggagctctgg gaggacccca ggcgctcgga gccgccgtta cgtaaccggc   1320
actcagagcc tccgaagacc ggaaggcccc gctcaggccc cggctcaggc ccggccccg    1380 gccccggccc cggcccgcc ccggcccggc cgggcagctg gtaggtgccg tgcgcaaccc   1440
tccggaagct gccgcccctt tccccttta tgggaatact tttttaaaa aaaaagagtt    1500 cgctggcgcc accccgtagg actggccgcc ctaaaaccgt gataaaggag ctgctcgcca   1560
cttctcactt ccgcttcctt ccagtaagga gtcgggtct tccccagttt tctcagccag    1620
gcggcggcgg cgactggcaa tgtttggcct caaaagaaac gcggtaatcg gactcaacct   1680
ctactgtggg ggggccggct tggggccgg cagcggcggc gccacccgcc cgggagggcg    1740
acttttggct acggagaagg aggcctcggc ccggcgagag atagggggag gggaggccgg   1800
cgcggtgatt ggcggaagcg ccggcgcaag ccccccgtcc accctcacgc cagactcccg   1860
gagggtcgcg cggccgccgc ccattggcgc cgaggtcccc gacgtcaccg cgaccccgc    1920 gaggctgctt ttcttcgcgc ccacccgccg cgcggcgccg cttgaggaga tggaagcccc   1980
ggccgctgac gccatcatgt cgcccgaaga ggagctggac gggtacgagc cggagcctct   2040
cgggaagcgg ccggctgtcc tgccgctgct ggagttggtc ggggaatctg gtaataacac   2100
cagtacggac gggtcactac cctcgacgcc gccgccagca gaggaggagg aggacgagtt   2160
gtaccggcag tcgctggaga ttatctctcg gtaccttcgg gagcaggcca ccggcgccaa   2220
ggacacaaag ccaatgggca ggtctgggc caccagcagg aaggcgctgg agaccttacg    2280
acgggttggg gatggcgtgc agcgcaacca cgagacggcc ttccaaggta agggggttca   2340
ttaatcgcca aggcctcact ccctttttc catctctccc cggactcacc cgccaagggt    2400
gggttggaaa ccgaaacgag tcagtgttga aacgtgtctc atcctattcc tgaagccaga   2460
atattctggc catgagtcat tgtttccgcc catcttgatt cttttggaaa tggcagctct   2520
tgttcaaaga ccggaaaggg tgggatgtca atttcaagtg gggtcaacct gagttctgta   2580
aatcccagta gcgattttcc cgccgcgggt gggcaggcga atcttgcgcc ggtttagaca   2640
aaggaggccg tgaggacctg catgcttttc tttctcaggc atgcttcgga aactggacat   2700
```

```
caaaaacgaa gacgatgtga aatcgttgtc tcgagtgatg atccatgttt tcagcgacgg   2760
cgtaacaaac tggggcagga ttgtgactct catttctttt ggtgcctttg tggctaaaca   2820
cttgaagacc ataaaccaag aaagctgcat cgaaccatta gcagaaagta tcacagacgt   2880
tctcgtaagg acaaaacggg actggctagt taaacaaaga ggctgggtaa gtttgcctta   2940
aggatgaaag gggccttgga gtggaagtag aatgaaggat ttttttaga gaggtgggga   3000 tatctaaagg ttttttatgac gcacggctgt ttgcaggctc taactaaagg accattgttt   3060
atttgatgtt gatttaagta gtggatcctt agagatagtg gtatggcggt cttgaattgt   3120
atcaaaaatc ttggttttct ctaggcaatt ttttgttcca attcagttga atactcttca   3180
gtggattcaa accatgaaaa aataagtcac caggggagga tagctgaaat aattcctaag   3240
gcggtgcctg ttttaatgga gaagatatgg ggtggagcct gcgttttaaa caaacccaga   3300
tctgatgcag gatgtactta actacgttga gaaaaactga tctgcgcaat tgaggcgtta   3360
ctgaaatatt aggtggtgga gatttgagaa taagggtttt cgtcttttac ctcatgggaa   3420
ctctggaagt cctttgtta ggataaatcc taataagacc aagatagtac tgtaaaatga   3480
agtttaatta tcatgggtcc ccgcttaaga aactgaagaa cttattttct ttttttgccc   3540
cggggtgaat aataattggt ttactattgc tttaggggga aaccttagat attttaattt   3600
accttctctc tggatagtag tgttgtaaga gagcagaaac ccatacttga aaatgtgctt   3660 ttctttttg ttttctagga tgggtttgtg gagttcttcc atgtagagga cctagaaggt   3720
ggcatcagga atgtgctgct ggcttttgca ggtgttgctg gagtaggagc tggtttggca   3780
tatctaataa gatagcctta ctgtaagtgc aatagttgac ttttaaccaa ccaccaccac   3840
caccaaaacc agtttatgca gttggactcc aagctgtaac ttcctagagt tgcaccctag   3900
caacctagcc agaaaagcaa gtggcaagag gattatggct aacaagaata aatacatggg   3960
aagagtgctc cccattgatt gaagagtcac tgtctgaaag aagcaaagtt cagtttcagc   4020
aacaaacaaa ctttgtttgg gaagctatgg aggaggactt ttagatttag tgaagatggt   4080
agggtggaaa gacttaattt ccttgttgag aacaggaaag tggccagtag ccaggcaagt   4140
catagaattg attacccgcc gaattcatta atttactgta gtgttaagag aagcactaag   4200
aatgccagtg acctgtgtaa aagttacaag taatagaact atgactgtaa gcctcagtac   4260
tgtacaaggg aagcttttcc tctctctaat tagctttccc agtatacttc ttagaaagtc   4320
caagtgttca ggacttttat acctgttata ctttggcttg gtttccatga ttcttacttt   4380
attagcctag tttatcacca ataatacttg acggaaggc cagtaattag ttatgaatat   4440
ggatatcctc aattcttaag acagcttgta aatgtatttg taaaaattgt atatatttt   4500 acagaaagtc tatttctttg aaacgaagga agtatcgaat ttacattagt ttttttcata   4560
cccttttgaa ctttgcaact tccgtaatta ggaacctgtt tcttacagct tttctatgct   4620
aaactttgtt ctgttcagtt ctagagtgta tacagaacga attgatgtgt aactgtatgc   4680
agactggttg tagtggaaca aatctgataa ctatgcaggt ttaaatttttc ttatctgatt   4740 ttggtaagta ttccttaggt ttttctttga aacctggga ttgagaggtt gatgaatgga   4800
aattctttca cttcattata tgcaagttttt caataattag gtctaagtgg agttttaagg   4860
ttactgatga cttacaaata atgggctctg attgggcaat actcatttga gttccttcca   4920
tttgacctaa tttaactggt gaaatttaaa gtgaattcat gggctcatct ttaaagcttt   4980
tactaaaaga ttttcagctg aatggaactc attagctgtg tgcatataaa aagatcacat   5040
caggtggatg gagagacatt tgatcccttg tttgcttaat aaattataaa atgatggctt   5100
```

```
ggaaaagcag gctagtctaa ccatggtgct attattaggc ttgcttgtta cacacacagg   5160
tctaagccta gtatgtcaat aaagcaaata cttactgttt tgtttctatt aatgattccc   5220
aaaccttgtt gcaagttttt gcattggcat cctttggattt cagtcttgat gtttgttcta   5280
tcagacttaa ccttttattt cctgtccttc cttgaaattg ctgattgttc tgctccctct   5340
acagatattt atatcaattc ctacagcttt ccctgccat ccctgaactc tttctagccc    5400
ttttagattt tggcactgtg aaaccctgc tggaaacctg agtgaccctc cctccccacc    5460
aagagtccac agacctttca tctttcacga acttgatcct gttagcaggt ggtaatacca   5520
tgggtgctgt gacactaaca gtcattgaga ggtgggagga agtcccttt ccttggactg    5580 gtatcttttc aactattgtt ttatcctgtc tttgggggca atgtgtcaaa agtcccctca   5640
ggaattttca gaggaaagaa cattttatga ggctttctct aaagtttcct ttgtatagga   5700
gtatgctcac ttaaatttac agaaagaggt gagctgtgtt aaacctcaga gtttaaaagc   5760
tactgataaa ctgaagaaag tgtctatatt ggaactaggg tcatttgaaa gcttcagtct   5820
cggaacatga cctttagtct gtggactcca tttaaaaata ggtatgaata agatgactaa   5880
gaatgtaatg gggaagaact gccctgcctg cccatctcag agccataagg tcatctttgc   5940
tagagctatt tttacctatg tatttatcgt tcttgatcat aagccgctta tttatatcat   6000
gtatctctaa ggacctaaaa gcactttatg tagttttttaa ttaatcttaa gatctggtta   6060
cggtaactaa aaaagcctgt ctgccaaatc cagtggaaac aagtgcatag atgtgaattg   6120
gtttttaggg gccccacttc ccaattcatt aggtatgact gtggaaatac agacaaggat   6180
cttagttgat attttgggct tggggcagtg agggcttagg acaccccaag tggtttggga   6240
aaggaggagg ggagtggtgg gtttataggg ggaggaggag gcaggtggtc taagtgctga   6300
ctggctacgt agttcgggca aatcctccaa aagggaaagg gaggatttgc ttagaaggat   6360
ggcgctccca gtgactactt tttgacttct gtttgtctta cgcttctctc agggaaaaac   6420
atgcagtcct ctagtgtttc atgtacattc tgtgggggt gaacaccttg gttctggtta    6480
aacagctgta cttttgatag ctgtgccagg aagggttagg accaactaca aattaatgtt   6540
ggttgtcaaa tgtagtgtgt ttccctaact ttctgttttt cctgagaaaa aaaaataaat   6600
cttttattca aatacagggt gtgatatggg tcttttctca tcgacgcctc ttttccttc    6660 cctctcttag gcaaaccttt tagagaagtc agctgagcaa atatgtacag gtgaattcaa   6720
agcaaaagcc tcacaaagtt gatttgcctt agagcaaagg acagttcctt tcttcaattc   6780
taattagagg tgttgggttt ttaattaaat atattactgc tgtacttaga ggagttctta   6840
aacctccaag taaaatcaaa aacctcttta aaatcaaaat ttctgtcttg atttatttat   6900
ttattatttt tttttttgaga tggagttttg ctcttgttgt ccaggctgga gtgcaatggc   6960
acgatctccg ctcaccgcaa cctccgcctc ccaggttcaa atgattctcc tgcctcagcc   7020
tcctgagtag ctgggaatac aggcatgcgc caccacaccc agataatttt gtattttag    7080 tagagatggg gtttctccgt gttggtcagg ctggtcttga actcccgacc tcaggtgatc   7140
tgcccacctc tgcctcccag agtgccagga ttacaggcgt gagccatcgc acccagcctc   7200
tgtcttgatt ttttttgaatc accaggtgtt ggtatgtttt gttttgtttt gtttgaggc    7260 acagtctcac tcttttgccc aggctagagt gcagtggggc aatctcggct cactgcaacc   7320
tcagcctccc gagtagctgg gattacaggt gcccgccacc atgccggct aatttttcta    7380 tttttggtag agacggggtt ttgccgtgtt ggtcaggctg gtcttgaagt cctgacctca   7440
```

```
gtgatccact cgcctcagcc gaagtgctgc gattacagac ctgagccact gcgcccagcc    7500
ttgatcttga ggtaagaggg tactgtacag cagttactct atcataacac ctaaataata    7560
cctaaagtta aagagttttg atgaagttct tggcagcagt gcttttcccc ttctgctttc    7620
caaaaggagg taaaagaag ccagtcaatt tcaaaaaccc ctatcctgct tttattttca     7680
gctaccttga aagtgagctg aatcaccatg gaaatgtgca aatgtgaggt ttgcatactt    7740
ggttttaagc cctgagcacc atatgctaat caggcaatca ggattctgtg cctccctgca    7800
gtcagttgca tttctattta aaagtgcatt ttggtttgga agccccttc tggagcctaa     7860 ctaccaaaag gcagcaactt tttgtatcat tacaaagaaa gctgtgtaag tgcactccca    7920
agcaaaggtg tggtaggaga gtagcagcca cagaggaccc aagcccaagt cttggcctga    7980
gttaagttag tgctattgct c                                              8001

<210> SEQ ID NO 6
<211> LENGTH: 2192
<212> TYPE: DNA
<213> ORGANISM: Mus musculus

<400> SEQUENCE: 6
ctccggtctg gagtcgcggc cttccccgct ccttcccctc agcctgcggc gtccgaccat      60
gtttggcctg cggagaaacg cggtcatcgg cttgaacctg tactgcggcg cgccagcct     120 cggcgcgggc ggcggttctc cggcagggc gcgcctggtg gccgaggagg ccaaggcgcg    180
gcgcgagggg ggaggggagg ccgccctgct gcccggcgcg cgggtggtcg cccggccgcc    240
gcccgtgggc gccgaggacc ccgacgtcac cgcgtcggcc gaaaggcggc tgcataagtc    300
gcccggcctc ctcgccgtgc cgcccgagga gatggccgcg tcggccgccg ccgccatcgt    360
gtctcccgag gaggaactgg acggctgcga gccggaggcg atcggcaagc gcccggccgt    420
gctgcccctc ctggagcgcg tgagcgaggc ggccaagagc tccggggccg acggctctct    480
gccctccacg ccgccgccgc ccgaggagga agaggacgac ctataccgcc agtcgctgga    540
gatcatctcg cgctacttgc gggagcaggc gaccggctcc aaggactcga agcctctggg    600
cgaggcgggc gcggcgggcc ggagagcgct ggagaccctg cggcgcgtgg gcgacggcgt    660
gcagcgcaac cacgagacgg ccttccaggg catgctccgg aaactggaca ttaaaaacga    720
aggcgatgtt aaatctttt ctcgagtaat ggtccatgtt tcaaagatg gcgtaacaaa      780 ctggggcagg attgtgactc ttatttcttt cggtgccttt gtggccaaac acttaaagag    840
cgtaaaccaa gaaagcttca tcgaaccatt agcagaaact atcacagatg ttcttgtaag    900
gacgaaacgg gactggcttg tcaaacaaag aggctgggat gggtttgtgg agttcttcca    960
cgtacaggac ctagaaggcg gcatcagaaa tgtgctgctg gcttttgcgg gtgttgctgg   1020
agtaggggct ggtctggcat atctaataag atagccttgt gagtgcaata ggggactctt   1080
aaagctccag ccaccaaact acatgcatct gtgaaaacat gtgtatttat gaaggtggac   1140
ttgaagctgc ccaggatttt aacagtccag ttctactgta gcaacatagc aaaaagaaag   1200
tggctacagg attgtggcta acaagaataa atacatggga aaagtgctcc ccctggaaga   1260
gtcactgtct gaatgaagca agttccctc tcagcaaaca ctgagaggcc atggagaagg    1320
acttctagaa tgaatgaaag gggtggatgg aaaggtttga tttcctatct agagatggaa   1380
gaggggccag tcatcaggct agtcacagag ctcaataaat atccattact ctgctcagag   1440
tgttgagaaa gaagccctaa ttaacaacgt tggtgacttg tgtaaaatgg atttgtaacc   1500
tacaagtcac caaacgatga ctagaagctg cagtgctgta caggaatgtg aagggaggcc   1560
```

-continued

```
tctgagcagt ccagggtgtg cttgacaaag tcccaagtgc tcaggacttt tagccctgtc    1620
tactttggct tggtttggat gattcttaag tttattagcc tagtgatggc caaaaagtac    1680
ttgacttaag gttcactaat tagttacaaa actgaacagc ctcgattttt aagaaaattt    1740
atgaaatgta tttgtctgta aaaattgtat atattttac agaaagtcta tttctttgaa     1800
cataagaggg aagtcttgga tttagttttt tccatacccc ttttgaaatt tgcagcttct    1860
ctagttagaa atgtatttct tacagctttt taagactttg tcatccgttc tagtgtatat    1920
gcagagcctg ttgtgtgtgt ggactggtta tagatttata actatgcagg gttaattatc    1980 caatctttt ttttgtattt aaagatcaca ggtagataga tgtaagacat ttgatcccct     2040
gttgacttac aaaattgtaa atggtaaagc aggctagagt cttaaccatg gtgctattca    2100
ctgggtttac ttgtttaaca caagtttata cctggtgtca ataaaacaaa tatgtatttc    2160
ttgtctaaaa aaaaaaaaaa aaaaaaaaaa aa                                  2192
```

```
<210> SEQ ID NO 7
<211> LENGTH: 3464
<212> TYPE: DNA
<213> ORGANISM: Mus musculus

<400> SEQUENCE: 7
```

```
ccacgcgtcc ggcctgcctc cggtctggag tcgcggcctt ccccgctcct tcccctcagc    60
ctgcggcgtc cgaccatgtt tggcctgcgg agaaacgcgg tcatcggctt gaacctgtac    120
tgcggcggcg ccagcctcgg cgcgggcggc ggttctccgg caggggcgcg cctggtggcc    180
gaggaggcca aggcgcggcg cgaggggggga ggggaggccg ccctgctgcc cggcgcgcgg    240
gtggtcgccc ggccgccgcc cgtggcgccc gaggacccccg acgtcaccgc gtcggccgaa    300
aggcggctgc ataagtcgcc cggcctcctc gccgtgccgc ccgaggagat ggccgcgtcg    360
gccgccgccg ccatcgtgtc tccggaggag gaactgacg gctgcgagcc ggaggccatc    420
ggcaagcgcc cggccgtgct gccccctctg agcgcgtgga gcgaggcggc caagagctcc    480
ggggccgacg gctctctgcc ctccacgccg ccgccgcccg aggaggaaga ggacgaccta    540
taccgccagt cgctggagat catctcgcgc tacttgcggg agcaggcgac cggctccaag    600
gactcgaagc ctctgggcga ggcgggcgcg cgggccgga gagcgctgga ccctgcgg     660 cgcgtgggcg acggcgtgca gcgcaaccac gagacggcct tccagggcat gctccggaaa    720
ctggacatta aaacgaagg cgatgttaaa tctttttctc gagtaatggt ccatgttttc    780
aaagatggcg taacaaactg gggcaggatt gtgactctta tttctttcgg tgcctttgtg    840
gccaaacact taaagagcgt aaaccaagaa agcttcatcg aaccattagc agaaactatc    900
acagatgttc ttgtaaggac gaaacgggac tggcttgtca acaaagagg ctgggatggg    960 tttgtggagt tcttccacgt acaggaccta gaaggcggca tcagaaatgt gctgctggct    1020
tttgcgggtg ttgctggagt aggggctggt ctggcatatc taataagata gccttgtgag    1080 tgcaatagg gactcttaaa gctccagcca ccaaactaca tgcatctgtg aaacatgtg     1140 tatttatgaa ggtggacttg aagctgccca ggattttaac agtccagttc tactgtagca    1200
acatagcaaa aagaaagtgg ctacaggatt gtgctaaca agaataaaata catgggaaaa    1260 gtgctccccc tggaagagtc actgtctgaa tgaagcaaag ttccctctca gcaaacactg    1320
agaggccatg gagaaggact tctagaatga atgaaagggg tggatggaaa ggtttgattt    1380
cctatctaga gatggaagag gggccagtca tcaggctagt cacaaagctc aataaatatc    1440
```

| | |
|---|---|
| cattactctg ctcagagtgt tgagagagaa gccctaatta caacgttggg tgacttgtgt | 1500 |
| aaaatggatt tgtaacctac aagtcaccaa acgatgacta gaagctgcag tgctgtacag | 1560 |
| gaatgtgaag ggaggcctct gagcagtcca gggtgtgctt gacaaagtcc caagtgctca | 1620 |
| ggacttttag ccctgtctac tttggcttgg tttggatgat tcttaagttt attagcctag | 1680 |
| tgatggccaa aaagtacttg acttaaggtt cactaattag ttacaaaact gaacagcctc | 1740 |
| gatttttaag aaaatttatg aaatgtattt gtctgtaaaa attgtatata ttttacaga | 1800 |
| aagtctattt cttgaacat aagagggaag tcttggattt agttttttc cataccctt | 1860 |
| tgaaatttgc agcttctcta gttagaaatg tatttcttac agcttttaa gactttgtca | 1920 |
| tccgttctag tgtatatgca gagcctgttg tgtgtgtgga ctggttatag atttataact | 1980 |
| atgcagggtt aattatccaa tcttttttt ttgtatttaa agatcacagg tagatagatg | 2040 |
| taagacattt gatccctgt tgacttacaa aattgtaaat ggtaaagcag gctagagtct | 2100 |
| taaccatggt gctattcact gggtttactt gtttaacaca agtttatacc tggtgtcaat | 2160 |
| aaaacaaata tgtatttctt gtctactaag gattgccaag cttgttttg aatttctgta | 2220 |
| ttggtctcta ggtgtagcct ttacttcctt tactgttggc gtgttatgct cccagttccc | 2280 |
| ctatagagtc gtctacactt cctccctgtg ctcttcactg gccattttag ttatctgcat | 2340 |
| tagaactctc accccaaccc cccaaaaact ttgaacctaa ataacccctc ccccatccta | 2400 |
| atcagagtca gcacagcttt cctgtcagag gataggaaca cttgctcttt gagccccgtg | 2460 |
| accgacagtg accagggatt ggcattcttg gattggcatg ctttccattg ttactttgtc | 2520 |
| tattttggta agaaaaacat caaaggtccc cttgggaatt tcaaaggttg gaaattatac | 2580 |
| gtttatactt ttattagttt gctccaagta tgactgtgtt cacttaagtt tagagaaaca | 2640 |
| ctgggttttg ctaaactcgg ttaacaaaag ccactggtaa ctgaaggtat ttaagctagg | 2700 |
| gtcatttgaa agcttcagcc tcagaatgtg acctttagtc agggctgcag ataaaaatag | 2760 |
| gcaggaatca aatgactaag aatgtaatag ggaagaagtg ccctgcctgc cagcttggga | 2820 |
| gtgatttgta cctgtgtatt tatccttgat catagtttgc ttatttatgt ttaactcttc | 2880 |
| ggacttcaga gcactttatg tagttgaata aaccctagag gttgaggtga ctaaaaggtt | 2940 |
| agcctctcat aacccagcca tggaagtttt gtttactagg agcctgactt cccagctcac | 3000 |
| aaagggtgaa atgaaagctg aagtacagac aggatcttag taggtatttt aggtccaggg | 3060 |
| ccatgaagac ttggagagcg cagtggctgg gcaaggggct gctttggagg gaagaagcat | 3120 |
| gtggtctgag tgctgactag atgaatagtt gaggcacatc cttcagagaa gagggaggg | 3180 |
| ctgcttggaa agatggctct cagcaaaatc tgtttgtctt acacgtctct cagggaaaaa | 3240 |
| acatgcagtc ttcaagcatc ttccatgtac attctatctg ggtgaacacc ttcattctgg | 3300 |
| tagagcacct aacactttaa cagctgttcc cgaaagggtt aggaccaact gcaagttaat | 3360 |
| gtgggttgta aatgttcccc taacttctgt ttcttctgaa gagaaaataa acttttttcc | 3420 |
| ccccaaaaaa aaaaaaaaaa aaaaaaaaaa aaaaaaaaaa aaaa | 3464 |

<210> SEQ ID NO 8
<211> LENGTH: 4369
<212> TYPE: DNA
<213> ORGANISM: Mus musculus

<400> SEQUENCE: 8

| | |
|---|---|
| gagtcgcggc cttccccgct ccttcccctc agcctgcggc gtccgaccat gtttggcctg | 60 |
| cggagaaacg cggtcatcgg cttgaacctg tactgcggcg gcgccagcct cggcgcgggc | 120 |

```
ggcggttctc cggcaggggc gcgcctggtg gccgaggagg ccaaggcgcg gcgcgagggg      180
ggagggggag gccgccctgc tgcccggcgc gcgggtggtc gcccggccgc cgcccgtggg      240
cgccgaggac cccgacgtca ccgcgtcggc cgaaaggcgg ctgcataagt cgcccggcct      300
cctcgccgtg ccgcccgagg agatggccgc gtcggccgcc gccgccatcg tgtctccgga      360
ggaggaactg gacggctgcg agccggaggc catcggcaag cgcccggccg tgctgcccct      420
cctggagcgc gtgagcgagg cggccaagag ctccggggcc gacggctctc tgccctccac      480
gccgccgccg cccgaggagg aagaggacga cctataccgc cagtcgctgg agatcatctc      540
gcgctacttg cgggagcagg cgaccggctc caaggactcg aagcctctgg gcgaggcggg      600
cgcggcgggc cggagagcgc tggagaccct gcggcgcgtg ggcgacggcg tgcagcgcaa      660
ccacgagacg gccttccagg gtaagcggcg cccgggccgg gccgggccgt gcgggaagag      720
ggaagagccg gagcctggct ctgcaaccag aatttctgg ctgtgagtca ttgtttccgc       780
ccatctggct gttgggttca agaccggaa agggtgggat gtcactgtcg gcgtggggtc       840
tgcctgactg ctctagagcc gggagagcac ggtcccctcg tcgtgggtgg cagaagggt       900 agtgccccgc tgcagacaaa ggaggccatg aggtttcttg cttttcttct caggcatgct      960
ccggaaactg acattaaaa acgaaggcga tgttaaatct ttttctcgag taatggtcca      1020
tgttttcaaa gatggcgtaa caaactgggg caggattgtg actcttattt ctttcggtgc     1080
ctttgtggcc aaacacttaa agagcgtaaa ccaagaaagc ttcatcgaac cattagcaga     1140
aactatcaca gatgttcttg taaggacgaa acggactgg cttgtcaaac aaagaggctg      1200
ggtaagttcg tcttgtgata taagggacc gtggagtgga atggggtgc aggattttgt       1260 gaaggagaag gcacctagag ggttttaca agtttctct ccggtttcag atttaattta       1320
tgtatctctt gttgcatgat gttggtcgtt gtaggtggta ggtccagaga aaaactcatt     1380
atgacggtct tgaattgtac caaaaggtct tgtattctgt aggttgtact tctaattcag     1440
ttggataatc ttcagagcag tggattcaaa ccgtgaagaa gtaagagtca cctgtgatga     1500
ctaaattaca tcccctcat tttaatcaaa tggataaggg gtagagcctg cattttagaa      1560
gttaataccc aaatacacca gctctggtgt aaggtgcact cattctcatt aggaaatacc     1620
catgggagaa atactacatg gggatggatc caaagagtgg ttggttatgg gccctgctca     1680
gtctgtgcaa aaataattga ggtgcaatac aactgctgta aggtaactgt tgtgtggtta     1740
ctcactggaa agaactccag aagtgtctct tgcatcccag aagtaggtaa ttggttcacc     1800
attgtttggg ggatatttta attcaccgtt tctctgtatg tagtgttaca acagcagaaa     1860
cccatacttg aaaatgtgct tttctttttt gttttctagg atgggtttgt ggagttcttc     1920
cacgtacagg acctagaagg cggcatcaga atgtgctgc tggcttttgc gggtgttgct      1980
ggagtagggg ctggtctggc atatctaata agatagcctt gtgagtgcaa tagggggactc    2040 ttaaagctcc agccaccaaa ctacatgcat ctgtgaaaac atgtgtattt atgaaggtgg     2100
acttgaagct gcccaggatt ttaacagtcc agttctactg tagcaacata gcaaaaagaa     2160
agtggctaca ggattgtggc taacaagaat aaatacatgg gaaagtgct ccccctggaa      2220 gagtcactgt ctgaatgaag caaagttccc tctcagcaaa cactgagagg ccatggagaa     2280
ggacttctag aatgaatgaa aggggtggat ggaaaggttt gatttcctat ctagagatgg     2340
aagaggggcc agtcatcagg ctagtcacaa agctcaataa atatccatta ctctgctcag     2400
agtgttgaga gagaagccct aattaacaac gttggtgact tgtgtaaaat ggatttgtaa     2460
```

| | | | | |
|---|---|---|---|---|
| cctacaagtc | accaaacgat | gactagaagc | tgcagtgctg | tacaggaatg tgaagggagg | 2520 |
| cctctgagca | gtccagggtg | tgcttgacaa | agtcccaagt | gctcaggact tttagccctg | 2580 |
| tctactttgg | cttggtttgg | atgattctta | agtttattag | cctagtgatg gccaaaaagt | 2640 |
| acttgactta | aggttcacta | attagttaca | aaactgaaca | gcctcgattt ttaagaaaat | 2700 |
| ttatgaaatg | tatttgtctg | taaaaattgt | atatatttt | acagaaagtc tatttctttg | 2760 |
| aacataagag | ggaagtcttg | gatttagttt | ttttccatac | cctttttgaaa tttgcagctt | 2820 |
| ctctagttag | aaatgtattt | cttacagctt | tttaagactt | tgtcatccgt tctagtgtat | 2880 |
| atgcagagcc | tgttgtgtgt | gtggactggt | atagatttta | taactatgca gggttaatta | 2940 |
| tccaatcttt | ttttttgta | tttaaagatc | acaggtagat | agatgtaaga catttgatcc | 3000 |
| cctgttgact | tacaaaattg | taaatggtaa | agcaggctag | agtcttaacc atggtgctat | 3060 |
| tcactgggtt | tacttgttta | acacaagttt | atacctggtg | tcaataaaac aaatatgtat | 3120 |
| ttcttgtcta | ctaaggattg | ccaagctttg | ttttgaattt | ctgtattggt ctctaggtgt | 3180 |
| agcctttact | tcctttactg | ttggcgtgtt | atgctcccag | ttcccctata gagtcgtcta | 3240 |
| cacttcctcc | ctgtgctctt | cactggccat | tttagttatc | tgcattagaa ctctcacccc | 3300 |
| aacccccca | aaactttgaa | cctaaataac | ccctccccca | tcctaatcag agtcagcaca | 3360 |
| gctttcctgt | cagaggatag | gaacacttgc | tctttgagcc | ccgtgaccga cagtgaccag | 3420 |
| ggattggcat | tcttggattg | gcatgctttc | cattgttact | ttgtctattt tggtaagaaa | 3480 |
| aacatcaaag | gtccccttgg | gaatttcaaa | ggttggaaat | tatacgttta tacttttatt | 3540 |
| agtttgctcc | aagtatgact | gtgttcactt | aagtttagag | aaacactggg ttttgctaaa | 3600 |
| ctcggttaac | aaaagccact | ggtaactgaa | ggtatttaag | ctagggtcat ttgaaagctt | 3660 |
| cagcctcaga | atgtgaccct | tagtcagggc | tgcagataaa | aataggcagg aatcaaatga | 3720 |
| ctaagaatgt | aatagggaag | aagtgccctg | cctgccagct | tgggagtgat ttgtacctgt | 3780 |
| gtatttatcc | ttgatcatag | tttgcttatt | tatgtttaac | tcttcggact tcagagcact | 3840 |
| ttatgtagtt | gaataaaccc | tagaggttga | ggtgactaaa | aggttagcct tcataacccc | 3900 |
| agccatggaa | gttttgttta | ctaggagcct | gacttcccag | ctcacaaagg gtgaaatgaa | 3960 |
| agctgaagta | cagacaggat | cttagtaggt | attttaggtc | cagggccatg aagacttgga | 4020 |
| gagcgcagtg | gctgggcaag | gggctgcttt | ggagggaaga | agcatgtggt ctgagtgctg | 4080 |
| actagatgaa | tagttgaggc | acatccttca | gagaagaggg | aggggctgct tggaaagatg | 4140 |
| gctctcagca | aaatctgttt | gtcttacacg | tctctcaggg | aaaaaacatg cagtcttcaa | 4200 |
| gcatcttcca | tgtacattct | atctgggtga | acaccttcat | tctggtagag cacctaacac | 4260 |
| tttaacagct | gttcccgaaa | gggttaggac | caactgcaag | ttaatgtggg ttgtaaatgt | 4320 |
| tcccctaact | tctgtttctt | ctgaagagaa | aataaacctt | tttcccccc | 4369 |

<210> SEQ ID NO 9
<211> LENGTH: 8001
<212> TYPE: DNA
<213> ORGANISM: Mus musculus

<400> SEQUENCE: 9

| | | | | |
|---|---|---|---|---|
| atgcatatgt | ggatgtcagg | aacagtggtt | aggagcccgt | ttctttccct tccagcacat | 60 |
| gggttccagg | gtttggcagc | aattgtcttt | acttgctgga | ccatcatcta tctccccatg | 120 |
| tcttttgttt | tgagcctccc | aagttctgga | actgaaggta | tgcagccaat ttacagggtt | 180 |
| ttaaacccaa | ggttttatgt | taggcaagca | ttctccaagt | aagccacatt tccagcttgc | 240 |

-continued

```
cacttactta tctatctatc tatctatcta tctatctatc tggtttgaga cagggtctca    300
acctttaac cctggctgat gggcgcttcc tatgtagacc aagtgtctta gtttgggtct    360
ctgttgctat ggcaaagcac cacaaccaaa agcagcttgg gagaaaaggg ttcattgggc    420
ttagcttgct tccacattac tgttcatcac tgaaggacat caggacagga actcaaacgg    480
ggcaggaacc tagaggcaga ggccatgggc aggagctgct aactggcttg tttcccatgg    540
cttgctcagc ctgttttctt acagaaccca ggaccgccag tccatggaat tccagcttgt    600
gtcaagttga tattaagtct aaccagtcca ccaaagatct tcaccgtttt atatggtgct    660
ggggatcaac ccaggacttc tacaagggta ggcaaattct ctaccaactg agttactccc    720
gtaaccatcc tttgttcatt ttagacagca ggctcatcat gtagccaaaa atgagtttta    780
aattgagtct cttgcctctg cctccccagg cctgggcaag ctcttctgcc aattgagcta    840
taggcctagc caccataaat ggctcatatt ttagacttttt actgtttggg gatagggtag    900
ggagctaggc tcttctggca gccagaggtc aactctggaa agtggtctca ctccttcatt    960
gttaggtggg ttctgtgtat tgaactcagg tctttagggc tgggtttcag gagcctttca   1020
ccagttgaat ctttcacagg ctccacataa ataaccccctt aatagctgtc catgaaaagt   1080
cattttggcc aggcagtgtg gggcacgcct ttaattccag cactcgggag gcagaggcag   1140
gaggatttct gagtttgagg ccagcctgat ctacagagtg agttccagtg cagccagggc   1200
tacacagaga aaccctgtct cgaaaaacaa aaaaacaaaa acaaaaaaca aaaaacaaaa   1260
aaaaccggaa cggaaagtca ttttggaaca cagggagtga gggctcacag tagaaaaatg   1320
acagagcagg actcccccta acttttaagc aaatcaatgg ttaatattcc tttgtgtatg   1380
agactggaga tgccctccct ggtttgctct tccagggttt aactcccagc acccacctgg   1440
aggcaggcac acaaccacaa atacacacaa acaaaaaagt gtttaagact ggtatgttat   1500
aaaaacacag caggtagtgc aacgagaaag gctaaggcag gactgcctaa cgttaggacc   1560
agcctgggct atgcagagtt ccagggcagc ttgaaattca aaaaccgaca cagatcagca   1620
ggcgttcccg agcaggaacc attccccggg aagccaagca cttggccagc cgggctgaga   1680
gttgtaccgg acaaaaaagc acaatccgtc cgcgagccaa ggccaggtac cgcgctccgc   1740
caaccgtagc cgcggaagcc gcgagagcgc tccggccgga agaggcgcgg agtggccggg   1800
ccagccctcc ggaaacgccc gcccctttcc ccttttacgg gaagtcctcg cctgcgtcag   1860
cacgccccta aggcggcggc agggaacggc cttcctcact cctgacttcc gcctgcctcc   1920
ggtctggagt cgcggccttc cccgctcctt cccctcagcc tgcggcgtcc gaccatgttt   1980
ggcctgcgga gaaacgcggt catcggcttg aacctgtact gcggcggcgc cagcctcggc   2040
gcgggcggcg gttctccggc aggggcgcgc ctggtggccg aggaggccaa ggcgcggcgc   2100
gagggggggag ggggaggccg ccctgctgcc cggcgcgcgg gtggtcgccc ggccgccgcc   2160
cgtgggcgcc gaggaccccg acgtcaccgc gtcggccgaa aggcggctgc ataagtcgcc   2220
cggcctcctc gccgtgccgc ccgaggagat ggccgcgtcg gccgccgccg ccatcgtgtc   2280
tccggaggag gaactggacg gctgcgagcc ggaggccatc ggcaagcgcc cggccgtgct   2340
gccccctcctg gagcgcgtga cgcgaggcgg caagagctcc ggggccgacg gctctctgcc   2400
ctccacgccg ccgccgcccg aggaggaaga ggacgaccta taccgccagt cgctggagat   2460
catctcgcgc tacttgcggg agcaggcgac cggctccaag gactcgaagc ctctgggcga   2520
ggcgggcgcg gcgggccgga gagcgctgga gaccctgcgg cgcgtgggcg acggcgtgca   2580
```

```
gcgcaaccac gagacggcct tccagggtaa gcggcgcccg ggccgggccg ggccgtgcgg    2640
gaagagggaa gagccggagc ctggctctgc aaccagaatt ttctggctgt gagtcattgt    2700
ttccgcccat ctggctgttg ggttcaaaga ccggaaaggg tgggatgtca ctgtcggcgt    2760
ggggtctgcc tgactgctct agagccggga gagcacggtc ccctcgtcgt gggtgggcag    2820
aagggtagtg ccccgctgca gacaaaggag gccatgaggt ttcttgcttt tcttctcagg    2880
catgctccgg aaactggaca ttaaaaacga aggcgatgtt aaatcttttt ctcgagtaat    2940
ggtccatgtt ttcaaagatg gcgtaacaaa ctggggcagg attgtgactc ttatttcttt    3000
cggtgccttt gtggccaaac acttaaagag cgtaaaccaa gaaagcttca tcgaaccatt    3060
agcagaaact atcacagatg ttcttgtaag gacgaaacgg gactggcttg tcaaacaaag    3120
aggctgggta agttcgtctt gtgatataaa gggaccgtgg agtggaaatg gggtgcagga    3180
ttttgtgaag gagaaggcac ctagagggtt tttacaaagt ttctctccgg tttcagattt    3240
aatttatgta tctcttgttg catgatgttg gtcgttgtag gtggtaggtc cagagaaaaa    3300
ctcattatga cggtcttgaa ttgtaccaaa aggtcttgta ttctgtaggt tgtacttcta    3360
attcagttgg ataatcttca gagcagtgga ttcaaaccgt gaagaagtaa gagtcacctg    3420
tgatgactaa attacatccc cctcatttta atcaaatgga taagggg tag agcctgcatt    3480 ttagaagtta atacccaaat acaccagctc tggtgtaagg tgcactcatt ctcattagga    3540
aatacccatg ggagaaatac tacatgggga tggatccaaa gagtggttgg ttatgggccc    3600
tgctcagtct gtgcaaaaat aattgaggtg caatacaact gctgtaaggt aactgttgtg    3660
tggttactca ctggaaagaa ctccagaagt gtctcttgca tcccagaagt aggtaattgg    3720
ttcaccattg tttgggggat attttaattc accgtttctc tgtatgtagt gttacaacag    3780
cagaaaccca tacttgaaaa tgtgcttttc tttttgttt tctaggatgg gtttgtggag     3840
ttcttccacg tacaggacct agaaggcggc atcagaaatg tgctgctggc ttttgcgggt    3900
gttgctggag taggggctgg tctggcatat ctaataagat agccttgtga gtgcaatagg    3960
ggactcttaa agctccagcc accaaactac atgcatctgt gaaacatgt gtatttatga     4020 aggtggactt gaagctgccc aggatttta cagtccagtt ctactgtagc aacatagcaa     4080
aaagaaagtg gctacaggat tgtggctaac aagaataaat acatgggaaa agtgctcccc    4140
ctggaagagt cactgtctga atgaagcaaa gttccctctc agcaaacact gagaggccat    4200
ggagaaggac ttctagaatg aatgaaaggg gtggatggaa aggtttgatt tcctatctag    4260
agatggaaga ggggccagtc atcaggctag tcacaaagct caataaatat ccattactct    4320
gctcagagtg ttgagagaga agccctaatt aacaacgttg gtgacttgtg taaaatggat    4380
ttgtaaccta caagtcacca aacgatgact agaagctgca gtgctgtaca ggaatgtgaa    4440
gggaggcctc tgagcagtcc agggtgtgct tgacaaagtc ccaagtgctc aggacttta     4500 gccctgtcta ctttggcttg gtttggatga ttcttaagtt tattagccta gtgatggcca    4560
aaaagtactt gacttaaggt tcactaatta gttacaaaac tgaacagcct cgatttttaa    4620
gaaaatttat gaaatgtatt tgtctgtaaa aattgtatat attttacag aaagtctatt     4680 tctttgaaca taagagggaa gtcttggatt tagttttttt ccatacccct ttgaaatttg    4740
cagcttctct agttagaaat gtattctta cagcttttta agactttgtc atccgttcta     4800
gtgtatatgc agagcctgtt gtgtgtgtgg actggttata gatttataac tatgcagggt    4860
taattatcca atctttttt tttgtattta aagatcacag gtagatagat gtaagacatt     4920 tgatccccctg ttgacttaca aaattgtaaa tggtaaagca ggctagagtc ttaaccatgg   4980
```

```
tgctattcac tgggtttact tgtttaacac aagtttatac ctggtgtcaa taaaacaaat    5040
atgtatttct tgtctactaa ggattgccaa gctttgtttt gaatttctgt attggtctct    5100
aggtgtagcc tttacttcct ttactgttgg cgtgttatgc tcccagttcc cctatagagt    5160
cgtctacact tcctccctgt gctcttcact ggccatttta gttatctgca ttagaactct    5220
caccccaacc cccccaaaac tttgaaccta ataaccccct cccccatcct aatcagagtc    5280
agcacagctt tcctgtcaga ggataggaac acttgctctt tgagcccgt  gaccgacagt    5340 gaccagggat tggcattctt ggattggcat gctttccatt gttactttgt ctattttggt    5400
aagaaaaaca tcaaaggtcc ccttgggaat ttcaaaggtt ggaaattata cgtttatact    5460
tttattagtt tgctccaagt atgactgtgt tcacttaagt ttagagaaac actgggtttt    5520
gctaaactcg gttaacaaaa gccactggta actgaaggta tttaagctag ggtcatttga    5580
aagcttcagc ctcagaatgt gacctttagt cagggctgca gataaaaata ggcaggaatc    5640
aaatgactaa gaatgtaata gggaagaagt gccctgcctg ccagcttggg agtgatttgt    5700
acctgtgtat ttatccttga tcatagtttg cttatttatg tttaactctt cggacttcag    5760
agcactttat gtagttgaat aaaccctaga ggttgaggtg actaaaaggt tagcctctca    5820
taacccagcc atggaagttt tgtttactag gagcctgact tcccagctca caaagggtga    5880
aatgaaagct gaagtacaga caggatctta gtaggtattt taggtccagg gccatgaaga    5940
cttggagagc gcagtggctg ggcaagggc  tgctttggag ggaagaagca tgtggtctga    6000
gtgctgacta gatgaatagt tgaggcacat ccttcagaga agaggagg   gctgcttgga    6060 aagatggctc tcagcaaaat ctgtttgtct tacacgtctc tcaggaaaa  aacatgcagt    6120 cttcaagcat cttccatgta cattctatct gggtgaacac cttcattctg gtagagcacc    6180 taacactttta acagctgttc ccgaaagggt taggaccaac tgcaagttaa tgtgggttgt    6240
aaatgttccc ctaacttctg tttcttctga agagaaaata aacctttttc cccccaaagt    6300
aaggtgtggt atgggtcttt tcttatcgcc ttcctctctt gtgcaagcct tttagggaag    6360
tcagttgaac aaatagaagt gaaataaaag caaaattcag tattgatttg ccttatggta    6420
aagaatatag gacctgtaat ttaaatttgt ggttaatgta ttcctgtttt aaactagttc    6480
ggtacgtttt tgggttgcgg gggagaatgc ttagcaccac acctggcttt tcattgaca    6540 agttccttgt atcttaaatt tattagtcaa ggttgacctt gaacatctat ggtgatcctg    6600
ctgtgctaaa gctgggatct tgggtgtgtt atccttgcct ctgcaggcag tgtacttgga    6660
gaaattagct ttgctcccca ccagccaagt gcaggctccc cttggaagtt aaccaagtac    6720
cagtgtgcat gaaaacaata acagatgcat tacaatggtt caccttgtaa tccaggttct    6780
cttctcccat ggtggcacct gggaggtgag actccagtca gccatctcaa cagccctatc    6840
ttgtgcgtgg ttttggtttt tcgaaacagg gttggtttct ctgtgtagcc ctaggctatt    6900
ctggaactct atagatcatg ctggcctgga atttagaaat ccacctgcct ctgccttcca    6960
agtgctggga ttaaaggcct gcacctccac tgcctggctt tgttttgttt ttataatgta    7020
aaaagattag caaagcaatg acacctttct tggttttcag tgcccttcc  aaggaggtaa    7080 gaataagctg gttagaacta tcctgccttt gtcacatccc ttgaaagggc aggggtgaat    7140
caccatggaa atgtgcaaat tgaggtttg  cataactggt tttcagccac aaatactaat    7200
catgcaaaca ggatctgcac cttctactta atcctgcctg ctttaacatc tgtcccttct    7260
tccatgggtt ttattagatg acagtaactt gattgtaaag ctgctttgtg gtaggcatcc    7320
```

```
tgactagctc atcataaccc cagcacttgg gctgagtcag aagtagctac tggagttcaa    7380
agctaacatg agctgtcctc taaaagtcgg agttggagtg gagcgctgaa gagatggctc    7440
tgagttaagt tcgcaacatc tgtgtaaggc aacccaaaat acctgattaa agctgcagga    7500
attgggatgg cctcttctac cttgatctct gttcacaaat tctcaacaga cataaaagtg    7560
aaaggaatga ctcacttgtt gggaatgtgt gtggttcagt ggttggacac aaacacaagg    7620
tcagcacaag tttgattcat aggattgaaa gagcagagct gtgtacaagt gtattattcc    7680
cttagcagag gcaagttggg acagtggcac ccaaggaaaa gctagactta ctcttaaatc    7740
ttgcttggca tatacctgta ctcccagcaa aaggattaca tcagattcaa ggtaagcctg    7800
tgctatgtga caagacccca acaaacgccc aaatcttgac ctagcttaag ttctgcccgg    7860
tactgttgtt aaggggaag ggggctgtac ttttgataca gagctaggct tgcgttgaac    7920
tttggacact tctgccttaa ccccttacct tgtatgccac catgatgccc ccccccttt    7980 tttttctttt tttgttttc g                                              8001

<210> SEQ ID NO 10
<211> LENGTH: 3396
<212> TYPE: DNA
<213> ORGANISM: Mus musculus

<400> SEQUENCE: 10
gagtcgcggc cttccccgct ccttcccctc agcctgcggc gtccgaccat gtttggcctg      60
cggagaaacg cggtcatcgg cttgaacctg tactgcggcg cgccagcct cggcgcgggc     120 ggcggttctc cggcaggggc gcgcctggtg gccgaggagg ccaaggcgcg gcgcgagggg     180
ggaggggagg ccgcccctgct gccggcgcg cgggtggtcg cccggccgcc gcccgtgggc     240
gccgaggacc ccgacgtcac cgcgtcggcc gaaaggcggc tgcataagtc gcccggcctc     300
ctcgccgtgc cgcccgagga gatgccgcg tcggccgccg ccgccatcgt gtctccggag     360
gaggaactgg acggctgcga gccggaggcc atcggcaagc gcccggccgt gctgcccctc     420
ctggagcgcg tgagcgaggc ggccaagagc tccggggccg acggctctct gccctccacg     480
ccgccgccgc ccgaggagga agaggacgac ctataccgcc agtcgctgga gatcatctcg     540
cgctacttgc gggagcaggc gaccggctcc aaggactcga agcctctggg cgaggcgggc     600
gcggcgggcc ggagagcgct ggagaccctg cggcgcgtgg gcgacggcgt gcagcgcaac     660
cacgagacgg ccttccaggg catgctccgg aaactggaca ttaaaaacga aggcgatgtt     720 aaatctttt ctcgagtaat ggtccatgtt ttcaaagatg gcgtaacaaa ctggggcagg     780
attgtgactc ttatttcttt cggtgccttt gtggccaaac acttaaagag cgtaaaccaa     840
gaaagcttca tcgaaccatt agcagaaact atcacagatg ttcttgtaag gacgaaacgg     900
gactggcttg tcaaacaaag aggctgggat gggtttgtgg agttcttcca cgtacaggac     960
ctagaaggcg gcatcagaaa tgtgctgctg cttttgcgg gtgttgctgg agtaggggct    1020
ggtctggcat atctaataag atagccttgt gagtgcaata ggggactctt aaagctccag    1080
ccaccaaact acatgcatct gtgaaaacat gtgtatttat gaaggtggac ttgaagctgc    1140
ccaggatttt aacagtccag ttctactgta gcaacatagc aaaaagaaag tggctacagg    1200
attgtggcta acaagaataa atacatggga aaagtgctcc ccctggaaga gtcactgtct    1260
gaatgaagca agttccctc tcagcaaaca ctgagaggcc atggagaagg acttctagaa    1320
tgaatgaaag gggtggatgg aaaggtttga tttcctatct agagatggaa gaggggccag    1380
tcatcaggct agtcacaaag ctcaataaat atccattact ctgctcagag tgttgagaga    1440
```

```
gaagccctaa ttaacaacgt tggtgacttg tgtaaaatgg atttgtaacc tacaagtcac    1500
caaacgatga ctagaagctg cagtgctgta caggaatgtg aagggaggcc tctgagcagt    1560
ccagggtgtg cttgacaaag tcccaagtgc tcaggacttt tagccctgtc tactttggct    1620
tggtttggat gattcttaag tttattagcc tagtgatggc caaaaagtac ttgacttaag    1680
gttcaccaat tagttacaaa actgaacagc ctcgattttt aagaaaattt atgaaatgta    1740
tttgtctgta aaattgtat atattttac agaaagtcta tttctttgaa cataagaggg    1800
aagtcttgga tttagttttt ttccataccc ttttgaaatt tgcagcttct ctagttagaa    1860
atgtatttct tacagctttt taagactttg tcatccgttc tagtgtatat gcagagcctg    1920
ttgtgtgtgt ggactggtta tagatttata actatgcagg gttaattatc caatcttttt    1980
tttttgtatt taaagatcac aggtagatag atgtaagaca tttgatcccc tgttgactta    2040
caaaattgta aatggtaaag caggctagag tcttaaccat ggtgctattc actgggttta    2100
cttgtttaac acaagtttat acctggtgtc aataaaacaa atatgtattt cttgtctact    2160
aaggattgcc aagcttttgtt ttgaatttct gtattggtct ctaggtgtag ccttacttc    2220 ctttactgtt ggcgtgttat gctcccagtt ccctataga gtcgtctaca cttcctccct    2280
gtgctcttca ctggccattt tagttatctg cattagaact ctcaccccaa ccccccaaa    2340 actttgaacc taaataaccc ctcccccatc ctaatcagag tcagcacagc tttcctgtca    2400
gaggatagga acacttgctc tttgagcccc gtgaccgaca gtgaccaggg attggcattc    2460
ttggattggc atgctttcca ttgttacttt gtctattttg gtaagaaaaa catcaaaggt    2520
cccttgggaa tttcaaaggt tggaaattat acgtttatac ttttattagt ttgctccaag    2580
tatgactgtg ttcacttaag tttagagaaa cactgggttt tgctaaactc ggttaacaaa    2640
agccactggt aactgaaggt atttaagcta gggtcatttg aaagcttcag cctcagaatg    2700 tgaccttag tcagggctgc agataaaaat aggcaggaat caaatgacta agaatgtaat    2760
agggaagaag tgccctgcct gccagcttgg gagtgatttg tacctgtgta tttatccttg    2820
atcatagttt gcttatttat gtttaactct tcggacttca gagcacttta tgtagttgaa    2880
taaaccctag aggttgaggt gactaaaagg ttagcctctc ataacccagc catggaagtt    2940
ttgtttacta ggagcctgac ttcccagctc acaaagggtg aaatgaaagc tgaagtacag    3000
acaggatctt agtaggtatt ttaggtccag ggccatgaag acttggagag cgcagtggct    3060
gggcaagggg ctgctttgga gggaagaagc atgtggtctg agtgctgact agatgaatag    3120
ttgaggcaca tccttcagag aagagggagg ggctgcttgg aaagatggct ctcagcaaaa    3180
tctgtttgtc ttcacgtct ctcagggaaa aacatgcag tcttcaagca tcttccatgt    3240
acattctatc tgggtgaaca ccttcattct ggtagagcac ctaacacttt aacagctgtt    3300
cccgaaaggg ttaggaccaa ctgcaagtta atgtgggttg taaatgttcc cctaacttct    3360
gtttcttctg aagagaaaat aaaccttttt cccccc                              3396
```

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11

```
cgtgtgtctg tgctagtccc                                                 20
```

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
ggcaacgtga acaggtccaa                                           20

<210> SEQ ID NO 13
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 13
gcccattgct ggacatgc                                             18

<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 14
agcccattgc tggacatgca                                           20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
ttgtcccagt cccaggcctc                                           20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
ctttccgttg gacccctggg                                           20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
gtgcgcgcga gcccgaaatc                                           20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 18
atccaagtgc tactgtagta                                          20

<210> SEQ ID NO 19
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-20
<223> OTHER INFORMATION: n is a, c, g, or t

<400> SEQUENCE: 19
nnnnnnnnnn nnnnnnnnnn                                          20

<210> SEQ ID NO 20
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 20
gccctccatg ctggcacagg                                          20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
agcaaaagat caatccgtta                                          20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
tacagaaggc tgggccttga                                          20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
atgcattctg cccccaagga                                          20

<210> SEQ ID NO 24
<211> LENGTH: 21
<212> TYPE: DNA
<213> ORGANISM: Artificial Sequence
<220> FEATURE:
<223> OTHER INFORMATION: Forward Primer

<400> SEQUENCE: 24
```

-continued caacggattt ggtcgtattg g                                        21

<210> SEQ ID NO 25
<211> LENGTH: 26
<212> TYPE: DNA
<213> ORGANISM: Artificial Sequence
<220> FEATURE:
<223> OTHER INFORMATION: Reverse Primer

<400> SEQUENCE: 25
ggcaacaata tccactttac cagagt                                   26

<210> SEQ ID NO 26
<211> LENGTH: 21
<212> TYPE: DNA
<213> ORGANISM: Artificial Sequence
<220> FEATURE:
<223> OTHER INFORMATION: Probe

<400> SEQUENCE: 26
cgcctggtca ccagggctgc t                                        21

<210> SEQ ID NO 27
<211> LENGTH: 19
<212> TYPE: DNA
<213> ORGANISM: Artificial Sequence
<220> FEATURE:
<223> OTHER INFORMATION: Forward Primer

<400> SEQUENCE: 27
gaaggtgaag gtcggagtc                                           19

<210> SEQ ID NO 28
<211> LENGTH: 20
<212> TYPE: DNA
<213> ORGANISM: Artificial Sequence
<220> FEATURE:
<223> OTHER INFORMATION: Reverse Primer

<400> SEQUENCE: 28
gaagatggtg atgggatttc                                          20

<210> SEQ ID NO 29
<211> LENGTH: 20
<212> TYPE: DNA
<213> ORGANISM: Artificial Sequence
<220> FEATURE:
<223> OTHER INFORMATION: Probe

<400> SEQUENCE: 29
caagcttccc gttctcagcc                                          20

<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30
tggaatcata ttggaacatg                                          20

<210> SEQ ID NO 31
<211> LENGTH: 20
<212> TYPE: DNA
<213> ORGANISM: Artificial Sequence

```
<220> FEATURE:
<223> OTHER INFORMATION: Forward Primer

<400> SEQUENCE: 31
ggcaaattca acggcacagt                                              20

<210> SEQ ID NO 32
<211> LENGTH: 20
<212> TYPE: DNA
<213> ORGANISM: Artificial Sequence
<220> FEATURE:
<223> OTHER INFORMATION: Reverse Primer

<400> SEQUENCE: 32
gggtctcgct cctggaagat                                              20

<210> SEQ ID NO 33
<211> LENGTH: 27
<212> TYPE: DNA
<213> ORGANISM: Artificial Sequence
<220> FEATURE:
<223> OTHER INFORMATION: Probe

<400> SEQUENCE: 33
aaggccgaga atgggaagct tgtcatc                                      27

<210> SEQ ID NO 34
<211> LENGTH: 23
<212> TYPE: DNA
<213> ORGANISM: Artificial Sequence
<220> FEATURE:
<223> OTHER INFORMATION: Forward Primer

<400> SEQUENCE: 34
tgttctagag acagccgcat ctt                                          23

<210> SEQ ID NO 35
<211> LENGTH: 21
<212> TYPE: DNA
<213> ORGANISM: Artificial Sequence
<220> FEATURE:
<223> OTHER INFORMATION: Reverse Primer

<400> SEQUENCE: 35
caccgacctt caccatcttg t                                            21

<210> SEQ ID NO 36
<211> LENGTH: 24
<212> TYPE: DNA
<213> ORGANISM: Artificial Sequence
<220> FEATURE:
<223> OTHER INFORMATION: Probe

<400> SEQUENCE: 36
ttgtgcagtg ccagcctcgt ctca                                         24

<210> SEQ ID NO 37
<211> LENGTH: 28
<212> TYPE: DNA
<213> ORGANISM: Artificial Sequence
<220> FEATURE:
<223> OTHER INFORMATION: Forward Primer

<400> SEQUENCE: 37
aagatctggt tacggtaact aaaaaagc                                     28
```

```
<210> SEQ ID NO 38
<211> LENGTH: 20
<212> TYPE: DNA
<213> ORGANISM: Artificial Sequence
<220> FEATURE:
<223> OTHER INFORMATION: Reverse Primer

<400> SEQUENCE: 38
gggcccctaa aaaccaattc                                              20

<210> SEQ ID NO 39
<211> LENGTH: 28
<212> TYPE: DNA
<213> ORGANISM: Artificial Sequence
<220> FEATURE:
<223> OTHER INFORMATION: Probe

<400> SEQUENCE: 39
tgtctgccaa atccagtgga aacaagtg                                     28

<210> SEQ ID NO 40
<211> LENGTH: 20
<212> TYPE: DNA
<213> ORGANISM: Artificial Sequence
<220> FEATURE:
<223> OTHER INFORMATION: Forward Primer

<400> SEQUENCE: 40
tccagggtgt gcttgacaaa                                              20

<210> SEQ ID NO 41
<211> LENGTH: 21
<212> TYPE: DNA
<213> ORGANISM: Artificial Sequence
<220> FEATURE:
<223> OTHER INFORMATION: Reverse Primer

<400> SEQUENCE: 41
tcatccaaac caagccaaag t                                            21

<210> SEQ ID NO 42
<211> LENGTH: 28
<212> TYPE: DNA
<213> ORGANISM: Artificial Sequence
<220> FEATURE:
<223> OTHER INFORMATION: Probe

<400> SEQUENCE: 42
tcccaagtgc tcaggacttt tagccctg                                     28

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
gaggccaaac attgccagtc                                              20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound
```

<400> SEQUENCE: 44
tttcttttga ggccaaacat                                                     20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
ggtgttatta ccagattccc                                                     20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
ccagacctgc ccattggctt                                                     20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
gctggtggcc ccagacctgc                                                     20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
gaagcatgcc ttggaaggcc                                                     20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
tgtccagttt ccgaagcatg                                                     20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
gaaaacatgg atcatcactc                                                     20

<210> SEQ ID NO 51

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
atcctgcccc agtttgttac                                               20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
agagtcacaa tcctgcccca                                               20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
ttagccacaa aggcaccaaa                                               20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
tggtttatgg tcttcaagtg                                               20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
gatgcagctt tcttggttta                                               20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
ggttcgatgc agctttcttg                                               20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
```
tttctgctaa tggttcgatg                                        20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
tttgtttaac tagccagtcc                                        20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
aacccatccc agcctctttg                                        20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
taggtcctct acatggaaga                                        20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
cacattcctg atgccacctt                                        20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
agcagcacat tcctgatgcc                                        20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
tccagcaaca cctgcaaaag                                        20

<210> SEQ ID NO 64
<211> LENGTH: 20
<212> TYPE: DNA

```
<213> ORGANISM: Artificial Sequence
<220> FEATURE:
<223> OTHER INFORMATION: Oligomeric Compound

<400> SEQUENCE: 64
ttagatatgc caaaccagct                                                    20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
tattgcactt acagtaaggc                                                    20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
gaagttacag cttggagtcc                                                    20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
tagggtgcaa ctctaggaag                                                    20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
gctaggttgc tagggtgcaa                                                    20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
tattcttgtt agccataatc                                                    20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
gggagcactc ttcccatgta                                                    20
```

```
<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
gtttgttgct gaaactgaac                                              20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
caaagtttgt tgttgctga                                               20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
ggaaattaag tctttccacc                                              20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
gaggaaaagc ttcccttgta                                              20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
gggaaagcta attagagaga                                              20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
atactgggaa agctaattag                                              20

<210> SEQ ID NO 77
<211> LENGTH: 20
<212> TYPE: DNA
<213> ORGANISM: Artificial Sequence
<220> FEATURE:
```

```
-continued

<223> OTHER INFORMATION: Oligomeric Compound

<400> SEQUENCE: 77
atattcataa ctaattactg                                              20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
gaattgagga tatccatatt                                              20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
tgtcttaaga attgaggata                                              20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
tcaaagaaat agactttctg                                              20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
ctacaaccag tctgcataca                                              20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
cagatttgtt ccactacaac                                              20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
catagttatc agatttgttc                                              20
```

-continued

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
gaatttccat tcatcaacct 20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
attgaaaact tgcatataat 20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
gtaagtcatc agtaacctta 20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
gcccaatcag agcccattat 20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
taaattaggt caaatggaag 20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
aagcctaata atagcaccat 20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound
```
<400> SEQUENCE: 90
tgacatacta ggcttagacc                                              20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
aagtatttgc tttattgaca                                              20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
actgaaatcc aaagatgcca                                              20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
aaagagttca gggatggcag                                              20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gagggtcact caggtttcca                                              20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
acagcaccca tggtattacc                                              20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
ggtttaacac agctcacctc                                              20

<210> SEQ ID NO 97
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 97
aactctgagg tttaacacag                                              20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
ttatcagtag cttttaaact                                              20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
tgaccctagt tccaatatag                                              20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
tttcaaatga ccctagttcc                                              20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
cagactaaag gtcatgttcc                                              20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
cctattttta aatggagtcc                                              20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
```
ggtccttaga gatacatgat                                               20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
tatgcacttg tttccactgg                                               20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
gccccaagcc caaatatca                                                20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
cccacagaat gtacatgaaa                                               20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
gtagttggtc ctaacccttc                                               20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
tagggaaaca cactacattt                                               20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
caaacccatc cttggaaggc                                               20

<210> SEQ ID NO 110
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 110
gcaaaagcca gcagcacatt                                              20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
aaggctatct tattagatat                                              20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
tgaagctttc aaatgaccct                                              20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
cagtcagcac ttagaccacc                                              20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
tggcttcagg aataggatga                                              20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
gaagcatgcc tgagaaagaa                                              20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
aggcaaactt acccagcctc                                              20
```

```
<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
aaaaaccttt agatatcccc                                               20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
tcaaataaac aatggtcctt                                               20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
atggtttgaa tccactgaag                                               20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
gacttccaga gttcccatga                                               20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
ttgaaaacat ggaccattac                                               20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
ccatctttga aaacatggac                                               20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound
```

<400> SEQUENCE: 123
gaaataagag tcacaatcct                                          20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
tgtttggcca caaaggcacc                                          20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
tctttaagtg tttggccaca                                          20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
gatagtttct gctaatggtt                                          20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
tttgtttgac aagccagtcc                                          20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
agcagcacat ttctgatgcc                                          20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
atgccagacc agcccctact                                          20

<210> SEQ ID NO 130

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
tagatatgcc agaccagccc                                                 20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
cttattagat atgccagacc                                                 20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
tcacaaggct atcttattag                                                 20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
tagtttggtg gctggagctt                                                 20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
ttttcacaga tgcatgtagt                                                 20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
tcataaatac acatgttttc                                                 20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
```
aatcctgggc agcttcaagt                                              20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
tcattcagac agtgactctt                                              20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
ttgcttcatt cagacagtga                                              20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
gaactttgct tcattcagac                                              20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
tcattcattc tagaagtcct                                              20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
tattgagctt tgtgactagc                                              20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
gagcagagta atggatattt                                              20

<210> SEQ ID NO 143
<211> LENGTH: 20
<212> TYPE: DNA

```
<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
caacactctg agcagagtaa                                              20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
ccattttaca caagtcacca                                              20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
taggttacaa atccatttta                                              20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
gacttgtagg ttacaaatcc                                              20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
gcacttggga ctttgtcaag                                              20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
taaaagtcct gagcacttgg                                              20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
tagacagggc taaaagtcct                                              20
```

```
<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
caagccaaag tagacagggc                                              20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151
ttggccatca ctaggctaat                                              20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
taattagtga accttaagtc                                              20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
agttttgtaa ctaattagtg                                              20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
tacagacaaa tacatttcat                                              20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
atttttacag acaaatacat                                              20

<210> SEQ ID NO 156
<211> LENGTH: 20
<212> TYPE: DNA
<213> ORGANISM: Artificial Sequence
<220> FEATURE:
```

-continued

```
<223> OTHER INFORMATION: Oligomeric Compound

<400> SEQUENCE: 156
tatacaattt ttacagacaa                                                 20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
tgttcaaaga aatagacttt                                                 20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
caaatttcaa aagggtatgg                                                 20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
tacatttcta actagagaag                                                 20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
agaaatacat ttctaactag                                                 20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
cacacaacag gctctgcata                                                 20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
aaccagtcca cacacacaac                                                 20
```

```
<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
aaatctataa ccagtccaca                                              20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
gatcaaatgt cttacatcta                                              20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
aattttgtaa gtcaacaggg                                              20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
tagcaccatg gttaagactc                                              20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
acttgtgtta aacaagtaaa                                              20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
gttttattga caccaggtat                                              20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 169
tttgttttat tgacaccagg                                              20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
aagaaataca tatttgtttt                                              20

<210> SEQ ID NO 171
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 171
ggcaatcctt agtagacaag                                              20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
gtaaaggaag taaaggctac                                              20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
agagcacagg gaggaagtgt                                              20

<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
ccagtgaaga gcacagggag                                              20

<210> SEQ ID NO 175
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 175
ccaagaatgc caatccctgg                                              20

<210> SEQ ID NO 176
<211> LENGTH: 20
```

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
ccaacctttg aaattcccaa                                               20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
catacttgga gcaaactaat                                               20

<210> SEQ ID NO 178
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
aacttaagtg aacacagtca                                               20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
tcagttacca gtggcttttg                                               20

<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
cctgactaaa ggtcacattc                                               20

<210> SEQ ID NO 181
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 181
ccaagctggc aggcagggca                                               20

<210> SEQ ID NO 182
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 182

```
ccaagtcttc atggccctgg                                                  20

<210> SEQ ID NO 183
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 183
attcatctag tcagcactca                                                  20

<210> SEQ ID NO 184
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 184
taccagaatg aaggtgttca                                                  20

<210> SEQ ID NO 185
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 185
ggtgctctac cagaatgaag                                                  20

<210> SEQ ID NO 186
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 186
ccacattaac ttgcagttgg                                                  20

<210> SEQ ID NO 187
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 187
tctagagcag tcaggcagac                                                  20

<210> SEQ ID NO 188
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 188
ggagcatgcc tgagaagaaa                                                  20

<210> SEQ ID NO 189
<211> LENGTH: 20
<212> TYPE: DNA
<213> ORGANISM: Artificial Sequence
```

-continued

```
<220> FEATURE:
<223> OTHER INFORMATION: Oligomeric Compound

<400> SEQUENCE: 189
caaaatcctg caccccattt                                                    20

<210> SEQ ID NO 190
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 190
agattatcca actgaattag                                                    20

<210> SEQ ID NO 191
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 191
gagctggtgt atttgggtat                                                    20

<210> SEQ ID NO 192
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 192
tgagcagggc ccataaccaa                                                    20

<210> SEQ ID NO 193
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 193
acattttcaa gtatgggttt                                                    20
```